United States Patent [19]

Yanaki et al.

[11] Patent Number: 5,538,728
[45] Date of Patent: Jul. 23, 1996

[54] HYDROPHILIC POLYMER-SILICATE MINERAL COMPLEX MATERIAL AND USE THEREOF

[75] Inventors: Toshio Yanaki; Tadahito Takahashi; Yoko Nagasawa; Michihiro Yamaguchi, all of Yokohama, Japan

[73] Assignee: Shiseido Company, Ltd., Tokyo, Japan

[21] Appl. No.: 46,840

[22] Filed: Apr. 14, 1993

Related U.S. Application Data

[63] Continuation of Ser. No. 688,513, Jun. 12, 1991, abandoned.

[30] Foreign Application Priority Data

Oct. 19, 1989 [JP] Japan ................................ 1-272324
Sep. 27, 1990 [JP] Japan ................................ 2-258542
Sep. 27, 1990 [JP] Japan ................................ 2-258543
Sep. 27, 1990 [JP] Japan ................................ 2-258544

[51] Int. Cl.$^6$ ...................................................... A61K 9/02
[52] U.S. Cl. ........................... 424/401; 424/683; 424/684; 424/78.02; 424/DIG. 15; 514/937; 514/944; 514/966; 514/925; 514/892
[58] Field of Search ............................. 424/401, DIG. 15, 424/683, 684, 78.02; 514/944, 966, 892, 925, 937

[56] References Cited

U.S. PATENT DOCUMENTS

| | | | |
|---|---|---|---|
| 4,333,461 | 6/1982 | Muller | 128/284 |
| 4,351,754 | 9/1982 | Dufré | 524/445 |
| 4,600,744 | 7/1986 | Libor et al. | 524/446 |
| 5,165,915 | 11/1992 | Tokubo et al. | 424/63 |

FOREIGN PATENT DOCUMENTS

| | | |
|---|---|---|
| 0172938 | 3/1986 | European Pat. Off. . |
| 0277244 | 8/1988 | European Pat. Off. . |
| 057981 | 6/1981 | Japan . |

Primary Examiner—Thurman K. Page
Assistant Examiner—Raj Bawa
Attorney, Agent, or Firm—Foley & Lardner

[57] ABSTRACT

A complex material of a hydrophilic polymer-silicate mineral comprising a carboxyl group containing hydrophilic polymer and a water swellable silicate mineral, and having a new absorption spectrum not existing in both starting materials in the IR-ray absorption spectrum within the range of 1000 to 1300 cm$^{-1}$, and pharmaceutical and cosmetic compositions comprising same.

13 Claims, 5 Drawing Sheets

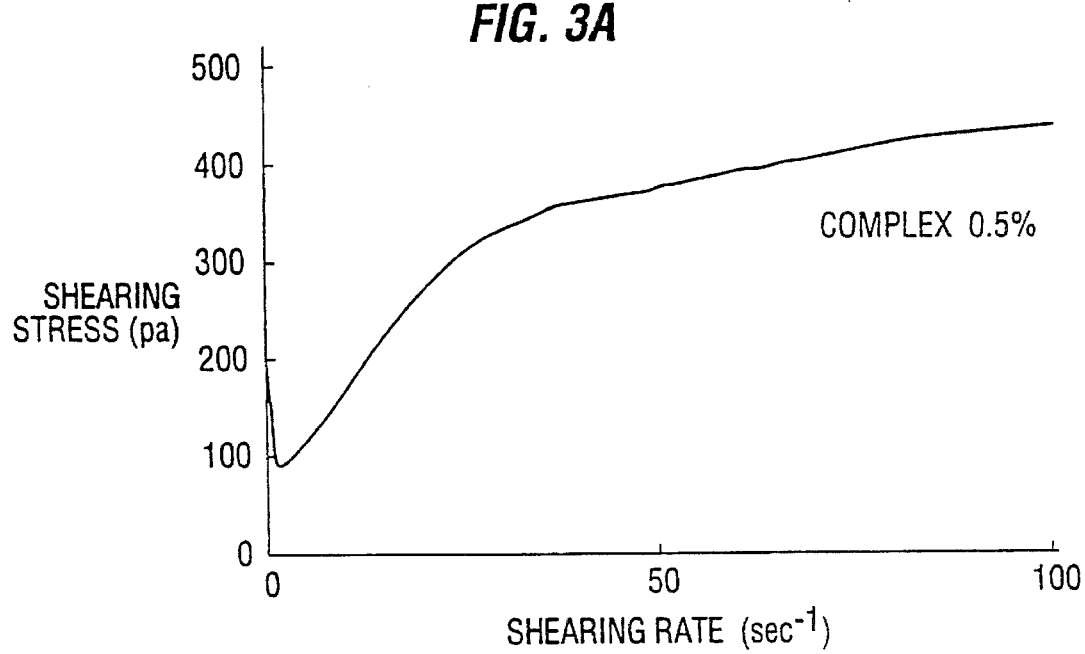
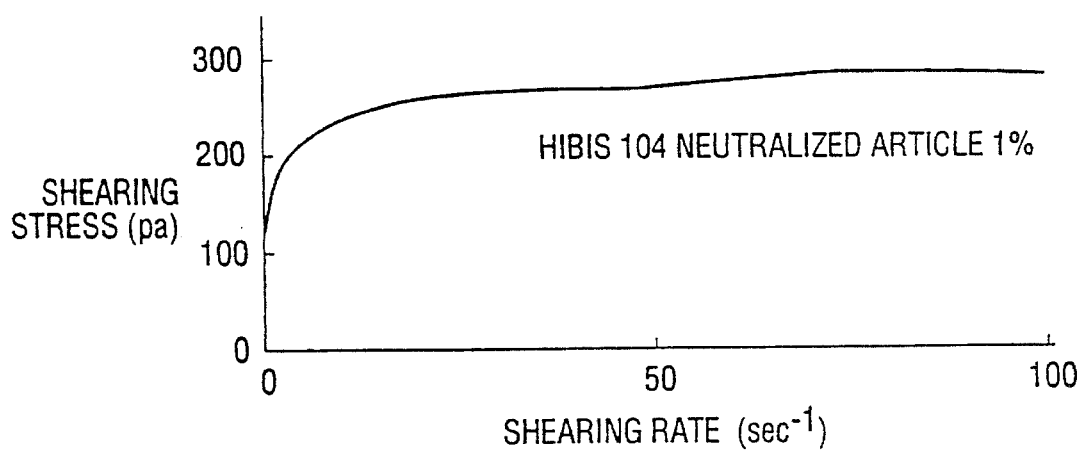
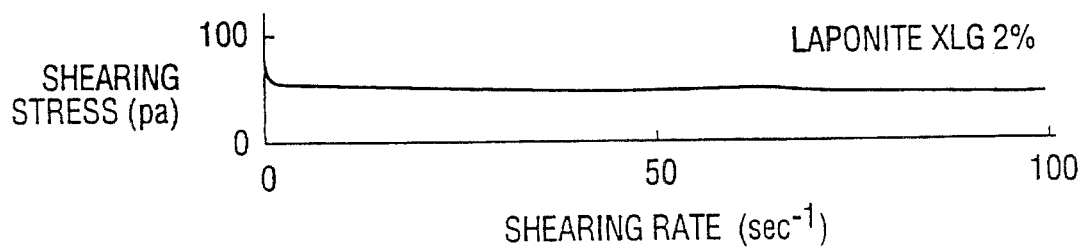

HYDROPHILIC POLYMER-SILICATE MINERAL COMPLEX MATERIAL AND USE THEREOF

This application is a continuation of Ser. No. 07/688,513 filed Jun. 12, 1991, now abandoned.

TECHNICAL FIELD

The present invention relates to a complex material comprising a carboxyl group containing a hydrophilic polymer and a water swellable silicate mineral. More particularly, it relates to the above-mentioned complex material having a very high water retentivity which is swelled and gelled by absorption of an aqueous substance to an extremely high degree when in contact with the aqueous substance, and further, the gel-like aromatic compositions, cosmetics, laxatives, rectal administration compositions, pharmaceutical compositions and skin ulcer external agents thereof.

BACKGROUND ART

As the material which is swelled and gelled by an absorption of an aqueous substance to a high degree when in contact with the aqueous substance, there may be included synthetic polymeric materials widely used for sanitary cotton, paper diapers, such as starch-acrylonitrile graft polymer hydrolyzates, starch-acrylic acid graft polymer neutralized products, saponified products of vinyl acetate-acrylate copolymers, hydrolyzate of acrylonitrile copolymers or acrylamide copolymers, or self-crosslinked type sodium polyacrylate.

Alternatively, among the substances which can be utilized in many fields, including pharmaceutical and cosmetics, those which cause a swelling and gelling of aqueous substances by an absorption of aqueous substances include natural polymers such as various polysaccharides, gelatin, synthetic polymers such as polyoxyethylene, acrylic acid type polymers, and inorganic mineral substances such as montmorillonite, silica. Particularly, among these, polyacrylic acid type polymers can further enhance the strength when gelled by mixing same with polyvalent oxides, polyvalent hydroxides, organic polyvalent metal compounds and salts thereof, or alumina and silica, as a crosslinking agent, and therefore are actually employed as a base for poultices. When this kind of gel is dried by a known method, when in contact with an aqueous substance, such an aqueous substance may be absorbed to some extent, but the stability and strength of the gel may be inferior with each substance alone, or the composition comprising the above-mentioned polymer and the above-mentioned crosslinking generally have too high a gel strength, whereby sometimes a gel having a sufficient aqueous substance will not be formed.

Emerson (J. Soil Science, 14, 52, 1963) reports that, when several % of a polyacrylic acid is added to a montmorillonite type soil, both form a complex material to become an improved soil which will not be scattered by rain.

In addition to the drawbacks as mentioned above of the composition or the complex material of the prior art, however, when directed to specific uses, for example, the synthetic polymeric materials used for the above-mentioned hygienic cotton and paper diapers probably has impurities such as unreacted monomers, polymerization initiators, crosslinking agents, and surfactants remaining therein, whereby their uses may be sometimes limited due to the characteristics of the starting materials themselves, and it has been difficult to direct them to uses for pharmaceuticals and cosmetics, for which a high safety is particularly demanded.

Also, concerning the substances used frequently for pharmaceutical and cosmetics among the compositions or complex materials as mentioned above, because of a weak gelling force thereof, drawbacks such that they were required to be formulated in large amounts, or that the gels were readily destroyed on account of presence of various salts, occurred.

Further, the complex material of polyacrylic acid and montmorillo-nite type soil reported by Emerson has a problem in that the swelling ability is low because of small content of polyacrylic acid, and the gel strength is extremely weak.

DISCLOSURE OF THE INVENTION

The present inventors, in view of the state of the art as described above, have made extensive studies in order to find substances which can be used in many fields, including particularly pharmaceutical and cosmetics, and have a high swelling ability and gel strength in combination, and as a result, have found that a complex material comprising a carboxyl group containing hydrophilic polymer and a water swellable silicate mineral formulates to exhibit a specific new IR-absorption spectrum not existing in either of these starting materials, can accomplish the above-mentioned object to complete the present invention. Therefore, in accordance with the present invention, there is provided a hydrophilic polymer-silicate mineral complex material comprising a carboxyl group containing hydrophilic polymer and a water swellable silicate mineral and having a new absorption spectrum not existing in these starting materials within the range of 1000 to 1300 $cm^{-1}$ in the IR-absorption spectrum. Also, there are provided particularly gel-like aromatic compositions, cosmetics, laxatives, rectal administration agents, pharmaceutical compositions having an improved water solubility, and skin ulcer external agents, based on the use of such a complex material.

BRIEF DESCRIPTION OF THE DRAWINGS

FIG. 3 is a graph showing the flow curves (dispersion medium: pure water) for the 0.5% gel of the complex material of Example 1 (Hibis weight fraction =0.85), the 1% gel of the Hibis 104 neutralized product, and the 2% gel of the Laponite XLG;

BEST MODE OF CARRYING THE INVENTION

Figure 1:
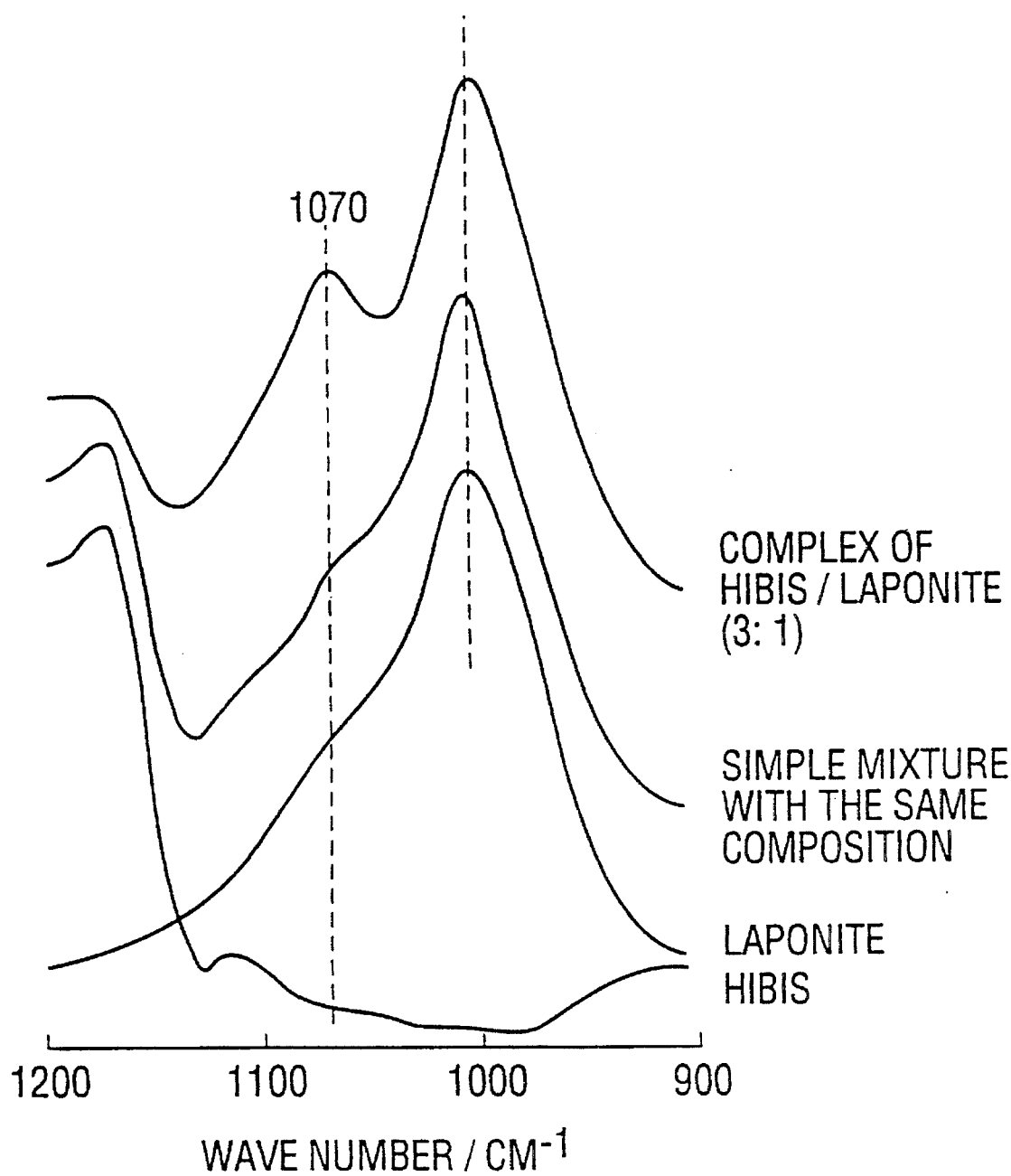
FIG. 1 shows the IR-absorption spectra of the complex material of the present invention comprising the acrylic acid type polymer and the layered silicate mineral of Example 1, the simple mixture with the same composition, Laponite, and Hibis, respectively.

The carboxyl group containing hydrophilic polymer to be used in the present invention is a polymer having carboxyl groups bonded directly or through lower alkylene group or lower alkyleneoxy group to the polymer backbone chain, or having carboxyl groups as the pendant groups, and refers to a polymer which is itself soluble or dispersible in an aqueous medium. As the polymer backbone, particularly backbone chains derived from addition polymerization of ethylenic monomers and sugar chains can be mentioned. As the lower alkylene group or lower alkyleneoxy group, specific examples include methylene, ethylene, propylene, isopropylene, butylene, methyleneoxy, ethyleneoxy, propyleneoxy, isopropyleneoxy and butyleneoxy groups. Therefore, the carboxyl group containing hydrophilic polymer includes a variety of polymers in accordance with the above definition, regardless of whether they are themselves known or not. More specifically, there are included, for example, the addition polymerization type polymers, including homopolymer, by using monomers such as acrylic acid, methacrylic acid, maleic acid, fumaric acid or iraconic acid or esters there of, or acrylonitrile or acrylamide or hydrolyzates thereof, copolymers of these monomers with vinylacetates or acrylonitrile or hydrolyzate thereof, or acidic polysaccharide such as carboxymethyl cellulose, hyaluronic acid, xanthin gum, gum arabic or alginic acid, etc. Among these, in the case of natural products, the extracts from natural products or fermented products with specific microorganisms themselves or those in which the molecular weights are modified by such means as hydrolysis, may be employed.

Also, the polymer obtained by graft polymerizing the above-mentioned carboxyl group containing monomer onto the neutral polysaccharides such as cellulose can be used as the polymer of the present invention. Specific examples of these include the polymers disclosed in Japanese Examined Patent Publication (Kokoku) No. 53- 46199, Japanese Unexamined Patent Publications (Kokai) Nos. 56-76419, 56-84701, and 60-31511, and U.S. Pat. No. 4,333,461.

Of the above-mentioned addition polymerization type polymers, particularly, poly(acrylic acid) and poly(methacrylic acid) homopolymer are preferable, preferably having (number or weight) average molecular weights of at least 500,000, more preferably over 1,000,000. Particularly, those having molecular weights of less than a 500,000 average molecular weight tend to be separated into poly(acrylic acid) or poly(methacrylic acid) and water swellable silicate mineral if left to stand for a long time, when the gel is formed in an aqueous substance, although the desired complex of the present invention can be formed.

On the other hand, the poly(acrylic acid) and the poly(methacrylic acid) are not particularly limited and may be straight chain or crosslinked type, but a complex material obtained by using a straight chain type as the starting material has a weaker gel strength during gelation than when using a crosslinked type as the starting material, and further, the fiber forming property remains even when formed into a gel. Therefore, it is more advantageous to use a crosslinked type as the poly(acrylic acid) and the poly(methacrylic acid). In this case, concerning the degree of crosslinking, the polymer may be one crosslinked under conditions wherein the weight % of the crosslinking agent based on respective monomers during the reaction falls within the range of 0.3 to 3.5%, and need not be crosslinked to such a high degree as employed in the poly(acrylic acid) and the poly(methacrylic acid) used in paper diaper. As an example, carboxypolymethylene or carboxylvinyl polymer set forth in the Component Standards of Quasi-drugs of Japanese Pharmacopoeia or the Standards of the Starting Materials for Cosmetics are included. As commercially available products, Hibis 104 (Wako Junyaku, molecular weight about 3,000,000), Hibis 103 (Wako Junyaku, molecular weight about 4,000,000), Carbopol 934 (Goodrich, molecular weight several 1,000,000) are included, as these have been confirmed to be safe when used to human bodies, and therefore, are particularly preferable for use with the complex of the present invention for the phrmaceuticals or cosmetics. It is preferable to use the acidic polysaccharide as specifically enumerated above, which are per se available for pharmaceutical and cosmetics.

The term water swellable silicate as used in the present specification and claims is used in a broad sense, and includes all kinds, provided it is a silicon dioxide containing a water swellable mineral naturally produced or synthesized. Therefore, the water swellable silicate mineral may include layered silicate minerals, typically swellable fine particulate silica as well as minerals belonging to the smectite family, the vermiculite family and the chlorite family. Specific examples of swellable fine particulate silica include Aerosol (trade mark, Nippon Aerosol), and commercial products thereof include Aerosol™ #200 and #303. The layered silicate mineral, for example, montmorillonite of the smectite family, forms one sheet of crystalline layer by bonding with lamination of silicate tetrahedral layer-alumina octahedral layer-silicate tetrahedral layer. Whereas, since the Al ion which is the center metal of the octahedral layer is partially substituted with Mg ion having smaller positive charge, the layer as a whole is negatively charged. The alkali metal ions corresponding to the negative charges exists between the layers to neutralize the charges of the crystalline layer. The exchangeable cations absorb a large amount of water between the layers, and therefore, the mineral has been known to exhibit a swellability even alone, and since these cations interact well with the above-mentioned carboxyl group containing hydrophilic polymers, it is preferable as the silicate mineral of the present invention.

Among these layered silicate minerals the smectite family including, in addition to the above-mentioned *montmorillonite* species, *paiderite* species, *saponite* species, *hectorite* species, *bentonite* species, *nontronite* species, and *sohconite* species is particularly preferable because it can give a complex material having on a good swellability in pure water and a high gel strength during gelation. As commercial products, Kunipia, Smecton (both from Kunimine Kogyo), Beagum (Vanderbilt), Laponite (Laporte), fluorotetrasilicon mica (Topy Kogyo), etc. can be utilized. When practicing the present invention, one or two or more kinds can be chosen from among these minerals, as desired.

The complex material of the present invention comprising the starting materials as described above is specific in having an IR-absorption at 1000 to 1300 cm$^{-1}$ not existing in these starting materials. Referring to an example of the complex material of the present invention comprising Hibis (Wako Junyaku) and Laponite (Laporte), as shown in the IR-absorption spectrum of said complex material measured with KBr tablet (FIG. 1), in addition to the absorption around 1000 cm$^{-1}$ due to the Si-O skeleton stretching vibration of the layered silicate mineral, a peak newly appears at around 1070 cm$^{-1}$. This absorption, as shown in the same Figure, does not exist in Hibis and Laponite which are the starting materials, and does not exist in a simple mixture thereof. Further, in the combinations of the acrylic acid type polymer and the layered silicate mineral other than this example, when the complex material of the present invention is formed, a peak appears at around 1040 to 1100 $cm^{-1}$, and therefore this peak can be considered as the absorption inherent to the complex material. The complex material of the present invention comprising the acrylic acid type polymer and the swellable fine particulate silica has new absorptions not found in either starting material, at around 1220 $cm^{-1}$ and 1225 $mm^{-1}$ as shown by the IR-absorption spectrum in FIG. 2. The IR-absorption spectrum thus newly appearing will vary in the absorption band thereof, depending on the starting materials chosen, but the complex material of the present invention can be specified by observation of the new absorption which appears in a region not existing in the starting materials. The mechanism of the appearance of this absorption has not yet been clarified, but may be considered to be due to a formation of a hydrogen bond between poly(acrylic acid) and/or poly(methacrylic acid) and the water swellable silicate mineral, or the ionic mutual interaction between the positive charge on the silicate mineral end surface and the negative charge of the dissociated carboxyl group.

The complex materials of the present invention are also characterized by a strong gel strength. For example, the hardness and gel strength of the complex material of the present invention when dispersed in pure water to 1% by weight, have the characteristics as shown in Table 1.

TABLE 1

|  | Hardness (−) | Gel strength (dyne/cm$_2$) |
| --- | --- | --- |
| Acrylic acid type polymer-layered silicate mineral complex | 8–65 | 15700–127000 |
| Polysaccharide-layered silicate mineral complex material | 1–30 | 1960–58800 |
| Acrylic acid type polymer-swellable fine particulate silica complex material | 5–60 | 9800–11800 |

Note:
Harness 1 corresponds to a gel (destruction) strength of 1960 (dyne/cm$^2$)

The complex material of the present invention as described above can be prepared from the respective corresponding starting materials according to a mixing-kneading method known per se. For example, first the carboxyl group containing hydrophilic polymer and the water-swellable silicate mineral are mixed in water until homogeneous. The concentrations thereof are not particularly limited because the properties of the homogeneous solution differ depending on the characteristics of the starting materials employed, but if the concentrations are too high, they become difficult to mix, and therefore, both are practically preferably 5% or lower. The mixing method can be practiced in conventional manner, but if the mixing is practiced at too high a shear rate, the polymer will be decomposed, and therefore, should be practiced under a relatively lower shear rate for a long time.

Next, the pH of the mixed aqueous solution is adjusted to 5 to 7, more desirably to 6.0 to 6.5, to effect a swelling and gelation. The pH at this time is not particularly limited, but this pH range may be considered to be advantageous for the formation of the complex material, because a particularly high gel strength is exhibited in this pH range.

Subsequently, the aqueous gel is dehydrated and dried and taken out as powder. The dehydration and drying method may be any of spray drying, lyophilization, solvent dehydration, etc., but solvent dehydration is the most efficient. Namely, to the aqueous gel is added alcohols or ketones as the precipitating agent or dehydrating agent, and the complex material is recovered by precipitation and taken out as powder. As alcohols or ketones, methanol, ethanol, n-propanol, iso-propanol, n-butanol acetone, methyl ethyl ketone or combinations thereof can be used.

The base used for the pH adjustment is not particularly limited, but alkali metal hydroxides, ammonia water, and water-soluble amines are preferable used. The purpose of the pH adjustment is to make a part of the carboxyl groups of the carboxyl containing hydrophilic polymer more readily dissociable into ions, thereby enhancing the swelling ability in pure water. The complex material will not be destroyed by such a pH adjustment. During such an adjustment of the pH, it is possible to add an organic or inorganic salt to give the salt-out effect, thereby making recovery of the precipitates in the subsequent step easier. In this case, it is advantageous to use a salt which is readily soluble in the alcohol or ketone to be added, so that no salt remains in the final complex material. The precipitates can be recovered by a conventional method such as centrifugation, filtration, and decantation.

Finally, the complex material, precipitated and recovered as described above, is transferred to the drying step, for which a drying method generally utilized, i.e., hot air drying or vacuum drying, can be utilized.

When it is desirable to avoid the use of an organic solvent, the aqueous gel formed in the above-mentioned pH adjustment step can be dried as such by a method such as freeze drying or spray drying, to obtain the complex material powder. Since the form of the present complex material can be varied from powder to sheet by choosing the concentration of the organic solvent and the drying method, these should be chosen depending on the purpose of use of the complex material.

The mixing ratio of these starting materials is not limited because it is varied depending on the kinds of polymer and the water swellable silicate mineral employed, but generally the mixing ratio of the carboxyl containing hydrophilic polymer and the water swellable silicate is 0.3 to 0.97 in terms of the weight fraction calculated on solids of the former. The gel strength of the present invention will be at a maximum within the range of the weight ratio of the polymer from 0.3 to 0.8. The complex material of the present invention thus obtained can be confirmed by an IR-absorption spectrum as described above, or by measuring the strength of the aqueous gel thereof, in some cases.

A particular feature of the characteristics of the complex material of the present invention is that the gel strength becomes about 2-fold that before drying, when a drying step is included in the preparation steps thereof. More specifically, the gel obtained by drying the gel after the pH adjustment, and dispersing it again into water to the same concentration, will have a value which is about 2-fold the gel strength before drying. The reason for this has not yet been clarified, but it is estimated that the intermolecular distance between the polymer and the water swellable silicate mineral is shortened by drying, whereby the hydrogen bonding is more developed, resulting in an increased gel strength.

Also, the complex material of the present invention has a swelling rate, swelling ability, and gel strength in combination which are equal to or higher than those of the synthetic polymeric materials presently used in sanitary cotton and paper diapers, for example, starch-acrylonitrild graft polymer hydrolyzate, hydrolyzate of acrylamide copolymer, self-crosslinking type sodium polyacrylate, etc. For example, when an acrylic acid polymer is used, it will be generally swelled to 200 to 800-fold in terms of weight ratio in water, and 30 to 100-fold in physiological saline.

On the other hand, poly(acrylic acid) of poly(methacrylic acid) and water swellable silicate mineral, which are starting materials of the complex material of the present invention, are both weak against salts, and when used as the base for a cream, etc., may cause a frequent water liberation to occur, but by a complex formation according to the present invention, a base which is stable at a broader salt concentration and in a broader pH region than the respective starting materials can be provided.

Also, as the starting materials, specific poly(acrylic acid), poly(methacrylic acid), hyaluronic acid, xanthin gum, gum arabic, which have been approved as additives in pharmaceuticals, can be combined to simply prepare the complex material, and therefore, materials (or base materials) suitably used particularly in the fields of pharmaceutical and cosmetics, where safety is demanded, can be provided.

More conveniently, the texture can be also controlled freely, from that approximate to a water swellable silicate mineral to that approximate to a polyacrylic acid, depending on the compositional ratio of the starting materials.

Therefore, it can be applied to an extremely wide range of applications, including bases for cosmetics such as creams, lotions, and aromatics, bases for pharmaceuticals such as styptic, hydrogels for pharmaceutical, laxatives, swellable contraceptives, and quiescent suppositorys and for sanitary uses such as paper diapers and other sanitary articles, soil improvers for agriculture and horticulture afforestation, water stoppage agents, plasma fractionation agents, dust preventives, dew formation preventives, deodorants, disposable pocket heaters, and gels for artificial seeds.

As one of the above, according to the present invention, by using the present complex material, a gel-like aromatic composition as described below is provided. More specifically, this is a gel-like aromatic composition comprising 1 to 99.0% by weight of a perfume, 0 to 90% by weight of an alcoholic organic solvent, 0 to 40% by weight of a nonionic surfactant, 0.1 to 90% by weight of the polymer-silicate mineral complex material of the present invention, and the balance of water.

In the prior art, for gel-like aromatic for room and toilette, various organic and inorganic compounds have been used as the thickening gelling agent for maintaining the forms thereof. For example, as organic compounds, metal soaps and agar, carrageenan, and polyacrylic acid resins are used, and as inorganic compounds, various layered silicate minerals and swellable fine particulate silica have been individually suitably used. However, aromatic containing a perfume in agar and carrageenan will be solidified to form a film on the surface during usage, whereby the volatilization of the perfume will be remarkably lowered. In the case of various layered silicate minerals and swellable fine particulate silica, a water liberation phenomenon occurs during storage, and water will be scattered when the seal is opened, thus having the drawback of contaminating clothing. On the other hand, aromatics using polyacrylic acid type resins used in paper diapers or sanitary articles have a drawback in that the volatilization of the perfume is very small.

In contrast, the gel-like aromatic composition using the complex material according to the present invention is free from the above-mentioned drawbacks.

The gel-like aromatic composition of the present invention comprises a complex material of a poly(acrylic acid) or poly(methacrylic acid)-water swellable silicate mineral, a perfume, an alcoholic organic solvent, a nonionic surfactant and water. The kind of the perfume in the present invention is not particularly limited, but, for example, those from the hydrocarbon type with a small polarity to the alcoholic type with a large polarity can be formulated. The alcoholic organic solvents can include methanol, ethanol, propanol, isopropanol, propylene glycol, 1,3-butylene glycol, 3-methyl-3-methoxybutanol, 3-methyl-1,3-butane diol or the like. The nonionic surfactant is not limited, provided that it can disperse, emulsify and solubulize the perfume, as exemplified by sorbitan esters, POE sorbitan esters, POE alcohol ethers, POE alkyl ethers, and POE castor oil derivatives. The poly(acrylic acid) or poly(methacrylic acid) may be either straight chain or crosslinked, and is not particularly limited.

Also, according to the present invention, a cosmetic comprising the present complex material formulated as the thickener is provided.

For the cosmetics, as the thickener, various polysaccharides, natural polymers such as gelatin, and synthetic polymers such as polyoxyethylene and polyacrylic acid have been primarily used. When cosmetics give a sticky feeling, such thickeners may be frequently a cause of such a feeling, and in such cases, a sticky feeling may be sometimes removed by using a water swellable silicate mineral such as montmorillonite and silica. However, since thickeners of the water swellable silicate mineral type have a poor stability, therefore there is a tendency for a water liberation with an elapse of time when formulated in cosmetics.

In contrast, by using the complex material according to the present invention as the thickener, a cosmetic which gives a conspicuous fresh feeling without stickiness can be obtained. Also, by using the complex material of the present invention prepared using the starting materials having previous examples of approval as the base for cosmetics, it can be also used without trouble with respect to safety.

The cosmetic according to the present invention can be thickened even with an extremely small amount and has a conspicuous freshness feeling without stickiness. The amount of the complex material to be formulated in the cosmetic is preferably 5.0% by weight or less, usually 1.0% by weight or less. Also, in the cosmetic of the present invention, in addition to the complex material, other components used conventionally for cosmetics such as organic and inorganic powders, polyhydric alcohol surfactants, preserving sterilizers, dyes, perfumes, and pharmaceuticals can be suitably formulated within the range which does not impair the effect of the present invention.

The dosage form of the cosmetic may be as desired, and can be a solubulized system, emulsified system, or powder dispersion system. The uses to which it is applied are wide and include basal cosmetics such as lotions, milky lotions, and creams, as a matter of course, and make-up cosmetics such as a foundation, and hair cosmetics.

Further, according to the present invention, there is provided a laxative having the present complex material formulated therein.

As the laxative, mucilaginous laxatives composed mainly of liquid paraffin or vegetable oil, infiltratable laxatives represented by surfactants, swellable laxatives such as agar, prisium seed, carboxymethyl cellulose, and methyl cellulose have been generally employed.

However, mucilaginous laxatives leak from the anus to contaminate clothing, dissolve vitamins A and D to inhibit the absorptions thereof, and inhibit the digestive action. On the other hand, infiltratable laxatives, when oily components are co-present, may be absorbed, and there is a fear that liver disorders may occur. Further, swellable laxatives, although having no local irritation action but, on the contrary exhibiting a mucilaginous-covering action, thus have an advantage in that they can be also used when there is an inflammatory disorder at enteric mucosa, have a drawback in that flatulence customarily accompanied with constipation is worsened at the initial stage of therapy, and a drawback in that they must be administered in a relatively larger dose.

In contrast, the laxative formulated with the complex material according to the present invention is highly swelled when borough into contact with even a very small amount of an aqueous substance such as body fluid, to form a soft gel, thereby acting effectively. Also, the complex material can be prepared simply by using a combination of starting materials which have previous approval as pharmaceutical additives, and therefore, may be considered to have no problem with respect to safety. Further, a particular feature of the present complex material is that it has specific properties of being substantially not swelled in an artificial gastric juice (Liquid 1 of Japanese Pharmacopoeia) but is swelled in an artificial enteric juice (Liquid 2 of Japanese Pharmacopoeia).

The laxative according to the present invention comprises the above-described complex material having the specific properties formulated therein. The complex material can be a swellable laxative even in a very small amount or alone, due to its high swelling ability, but by a combination with various pharmaceutical and additives to be formulated in other conventional laxatives, a further promotion of muciliaginous-covering action and reduction of local irritation can be effected. Thus, the materials which can be formulated with the carboxyl containing hydrophilic polymer-water swellable silicate mineral complex material include fluid paraffins, various vegetable oils, dioctyl sodium sulfossucinate, polocsalcol, agar powder, Ispagule powder, prisium seed, methyl cellulose, carboxymethyl cellulose, mannan, otherwise various vitamins, and excipitents.

The dosage form is not particularly limited, and granules, tablets, powder, and capsules can be used.

Further, according to the present invention, there is provided a rectal administration composition formulated with the present complex material.

The rectal formulation preparation is adapted to be used for effecting not only a local action but also a systemic action, by making use of its pharmaceutical advantages. When a local action is required, it is used for hemorrhoids, conticipation, and enteral cleaning. When a systemic action is required, for example, extremely various pharmaceutical can be administered as the rectal administration preparation for use in antipyretic, analgesic, anticonvulsant, antieplectic, antiemetic, tranquilizer, circulatory organs, peripheral nerve, antihistamine, hemostasis, antitumor, and antibiotics. However, among pharmaceuticals, some have a low absorption ratio from the rectum, posing a problem in bioavailability. The availability of a pharmaceutical from a rectal administration preparation depends on the effective concentration of the pharmaceutical itself within the rectal cavity, its transition with a lapse of time, and for this reason, various attempts have been made to ameliorate the releasability and persistence of the pharmaceutical from a rectal administration preparation. There are also known such attempts a formulation of a polyacrylic acid metal salt as disclosed in Japanese Unexamined Patent Publication (Kokai No. 54-26325), a formulation of a gel-forming agent such as polygum as disclosed in Japanese Unexamined Patent Publication No. 59-55817, a formulation of a water swellable silicate mineral as disclosed in Japanese Unexamined Patent Publication (Kokai) No. 2-15024, and an implement to be mounted within the anus (Japanese Unexamined Patent Publications (Kokai) No. 49-6116, 58-208213).

However, the attempts to formulate poly(acrylic acid) metal salts, gel-forming agents, and water swellable silicate minerals cannot be said to be satisfactory with respect to the persistency and releasability thereof. The attempt to mount an implement within the anus had the drawback of giving pain or a foreign feeling to patients.

In contrast, in the present invention, by utilizing the excellent water absorptive action and high safety to living bodies of the complex material comprising the above-mentioned carboxyl containing hydrophilic polymer and the water swellable silicate mineral mentioned above, the present composite is formulated into the rectal administration composition, whereby a residence in the rectal cavity is imparted, and a persistency and releasability of the pharmaceutical can be synergetically ameliorated.

The rectal administration composition according to the present invention is characterized by formulating the complex material of the present invention having the above-mentioned specific properties. The amount of the complex material formulated into the rectal administration composition should be desirably 0.01 to 70% by weight. Here, if the amount of the complex material formulated is extremely small, a sufficient water swellability can not be obtained in the preparation formed, while if it is too much, the preparation formed will be undesirablye brittle and unstable.

The rectal administration composition in the present invention can be formed into a preparation in conventional manner together with a pharmaceutical and a base in addition to the complex material comprising, for example, a poly(acrylic acid) and a water swellable silicate mineral. If necessary, various additives such as preservatives, stabilizers, colorants, surfactants, antiseptics, extenders, and antioxidants can be also formulated.

The rectal formulation composition in the present invention can be administered to patients in the form of a rectal suppository formed in a conventional manner, soft capsules for a rectal administration, or dosage form to be administered by a syringe for a rectal administration.

The pharmaceutical to be used in the present invention is not particularly limited, but examples of the pharmaceutical for rectal administration generally include steroid hormones such as hydrocortisone, hydrocortisone acetate, prednisolone, methylprednisolone, prednisolone acetate, hydrocortisone acetate propionate, prednisolone valerate acetate, dexamethasone, betamethasone, triamcinolone, chlobetazone butyrate, chlobetazole propionate, fluosinonide, dexamethasone acetate, betamethazone valerate, triamcinolone acetonide, etc.; antiphlogistic analgesics such as aspirin, salicylic acid, acetaminophen, methyl salicylate, glycol salicylate, mefenamic acid, fluefenamic acid, indometacin, diclofenac, ketoprofen, ibuprofen, flurbiprofen, fenbufen, bufexamac, pyroxicam, oxyphenbutazone, mepirizole, ibuprofen-piconol, kuridanac, phenylbutazon, naproxen, glycyrrhizin, glycyrrhizic acid, azulene, camphor, thymol, l-menthol, etc.; local anesthetics such as dibucaine hydrochloride, ethyl etc.; animal fats such as tallow, lard, wool fat, etc.; oils and fats obtained by processing treatments such as hardening, ester exchange, fractionation, distillation, etc. of these animal and vegetable oils and fats; mineral oils such as petrolatum, paraffins, fluid paraffins, silicone oils, etc.; higher fatty acids such as stearic acid, oleic acid, lauric acid, myristic acid, palmitic acid, etc.; higher alcohols such as cetanol, lauryl alcohol, stearyl alcohol, etc.; waxes such as wood was, whale wax, honey was, beeswax, etc.; natural and synthetic fatty acid triglycerides such as Wittepsol, Saposier, Pharmasol, ODO, Panacete, Coconade, Migriol, etc.; and so on. On the other hand, as the water soluble base, for example, polyethylene glycol, polypropylene glycol, glycerine, glycero-gelatin, etc. can be included, and the above bases can be used either single or in combination of two or more kinds.

The reason why a residence can be retained in the present invention is considered to be due to the fact that the complex material of a carboxyl group containing hydrophilic polymer and a water swellable silicate mineral according to the present invention has a water swelling action, and that its specific gravity is larger than 1, whereby the base becomes heavier than water and consequently, a diffusion from within rectal cavity can be suppressed. Also, when this fact is considered from the pharmaceutical point of view, since the present rectal administration composition resides below the rectum, an initial passing effect in the liver can be avoided, and consequently a bioavailability of the pharmaceutical is enhanced, and further, the pharmaceutical is aminobenzoate, procaine hydrochloride, lidocaine, benzocaine, procaine, dibucaine, tetracaine hydrochloride, lidocaine hydrochloride, teecaine, benzyl alcohol, promoxine hydrochloride, catacaine hydrochloride, butanicaine hydrochloride, piperocaine hydrochloride, chlorobutanol, etc.; narcotic tranquilizers such as barbital, amobarbital, amobarbital sodium, phenobarbital, phenobarbital sodium, secobarbital sodium, benzobarbital calcium, hexobarbital, trichlophos, bromovalerylurea, glutethimide, metacalon, perulapin, nitrazepam, flurazepam hydrochloride, flunitrazepam, estazolam, etc.; anti-malignant tumor agents such as cyclophosphamide, busulfan, p-aminosalicylic acid, 5-fluorouracil, mercaptopurine, tegafur, methotrexate, azathioprine, vinblastin sufat, doxorubicin hydrochloride, bleomycin hydrochloride, mitomycin C, cyclosporin, L-asparaginase, cysplastin, etc.; antibiotics such as chloramphenicol, cephamethazole, bacitracin, penicillin, cephalexin, tetracycline, streptomycin, nystatin, erythromycin, fradiomycin sulfate, etc.; blood circulation promotors such as tocopherol acetate, benzyl nycotinate, trazoline, verapamil, caffeine, cyclanderate, acetylcholine, tocopherol nicotinate; and so on. The above pharmaceuticals can be used either singly or in combination of two or more kinds.

The base to be used in the present invention may be either oily or water soluble, and examples of oily base may include vegetables oils such as cacao fat, palm fat, laurin fat, cinnamon fat, coconut oil, olive oil, soybean oil, repeseed oil, camellia oil, coconut oil, peanut oil, avocado oil, corn oil, sesame oil, absorbed gradually, whereby the persistency is also improved.

The rectal administration composition can be also applied as a vaginal suppository, due to the characteristics possessed thereby.

Further, according to the present invention, there is provided a pharmaceutical composition having a difficult-to-solubulize pharmaceutical formulated with the present complex material.

A difficult-to-solubulize pharmaceutical, when administered to or coated on a living body, has a low solubility into a digestive juice or skin fat, and therefore, the pharmacological activity can be effectively absorbed only with difficulty. Therefore, various attempts have been made to ameliorate the absorbability of difficult-to-solubulize pharmaceuticals. For example, attempts have been made to enhance the absorbability of the pharmaceutical by embedding them in liposome bases or incorporating difficult-to-solubulize pharmaceutical in a hydrogenated phospholipid matrix (Japanese Unexamined Patent Publication (Kokai) No. 61-172832).

However, although the method using liposome and hydrogenated phospholipid may have an excellent biocompatibility, it has no persistency at a high solubility, and further, when formulated in an external agent, drawbacks arise in that the amount of the pharmaceutical distributed on the skin fat is small, and the amount absorbed by the skin is also small.

In contrast, the pharmaceutical composition according to the present invention, by utilizing the excellent water absorptive action as well as a high safety to living body of the composition comprising a carboxyl group containing hydrophilic polymer and a water swellable silicate mineral, to enable the difficult-to-solubulize pharmaceutical to be included in the complex material, a composition exhibiting an excellent solubility, permucosal and percutaneous absorption can be obtained.

The pharmaceutical composition according to the present invention is characterized by formulating the above-described complex material having specific properties with a difficult-to-solubulize pharmaceutical.

In the present invention, difficult-to-solubulize pharmaceuticals are those which are "slightly difficult-to-solubulize", "difficult-to-solubulize", "extremely difficult-to-solubulize", and "substantially insoluble", as defined in the Japanese Pharmacopoeia, including specifically coronary blood vessel vasodilators such as nifedipine, dipyridamole, prenylamine lactate, efloxate, etc.; antiepileptis such as phenytoin, phenacemide, ethylphenacemide, ethotoin, primidone, phensuccimide, nitrazepam, chlonazeban, carbamazepine, etc., antibiotics such as griseofulvin, tolunaphtate, etc.; skeletal muscle relaxants such as chlosobzaone, phenopropamate, etc., antihistamines such as diphenhydramine, metakidin, etc.; caridacs such as digoxin, digitoxin, cobidekarenon, etc.; arrhythmics such as phenytoin, disophramide, etc.; diuretics such as polythiazide, spironolactone, chlorotaridone, etc.; hypotensors such as decerupidine, meptame, reserpine, meptamate, etc.; hormones such as prostaglandin F, $2\alpha$ danasol, mepitiostane, etc., which are substantially insoluble in water, or have a very low solubility if dissolved to some extent, or a very slow dissolving rate. The difficult-to-solubulize pharmaceutical employed may be either a solid or a liquid.

In the following, the method of preparing the pharmaceutical composition of the present invention is described with reference to an example of poly(acrylic acid) and a water swellable silicate mineral.

First, a difficult-to-solubulize pharmaceutical is dissolved in an organic solvent and the complex material of a poly(acrylic acid) and a water swellable silicate mineral according to the present invention is dispersed into the solution, is thoroughly stirred, and the organic solvent is then removed, followed by a thorough drying, to give a pharmaceutical composition of the present invention. One or two more kinds of difficult-to-solubulize pharmaceutical may be dissolved at the same time in a solvent, depending on the desired preparation. The method of removing the solvent preferably uses an evaporator or a vacuum dryer. The method of removing the solvent by filtration is not preferable, because even the difficult-to-solubulize pharmaceutical may be discharged. As the organic solvent, those generally employed, such as ethanol, methanol, acetone, etc. may be used, but a solvent species and a solvent amount capable of dissolving the pharmaceutical uniformly are required. The temperature at which the complex material is dispersed is not limited, provided it is a temperature at which the difficult-to-solubulize pharmaceutical can be dissolved, and room temperature may be sufficient depending on the kind of pharmaceutical.

In the pharmaceutical composition of the present invention, the ratio of the difficult-to-solubulize pharmaceutical based on the complex material of a poly(acrylic acid) and a water swellable silicate mineral is not particularly limited, but when it exceeds 10%, the difficult-to-solubulize pharmaceutical will be insufficiently included, whereby crystals of the pharmaceutical may be precipitated, and therefore, is preferably 10% or less. The inclusion ability of the pharmaceutical composition of the present invention can be controlled by varying the kind or formulation ratio of the poly(acrylic acid) and the water swellable silicate mineral during the preparation of the complex material, and consequently, the dissolving rate of the pharmaceutical can be controlled. The pharmaceutical composition of the present invention can be also prepared by mixing the complex material with a difficult-to-solubulize pharmaceutical in a base, without problems.

In the pharmaceutical composition of the present invention, in addition to the essential components as described above, there can be suitably added other components conventionally used in pharmaceuticals, quasi-drugs, cosmetics, foods, agricultural medicines, etc., including, for example, vitamin A's such as vitamin A oil, retinol, retinol acetate, etc.; vitamin $B_2$'s such as riboflavin, riboflavin acetate, flavin adenine dinucleotide, etc.; vitamin $B_6$'s such as pyridoxine hydrochloric acid, pyridoxine dioctanoate; vitamin C's such as L-ascorbic acid, dipalmitic L-ascorbate, sodium L-ascorbic acid-2-sulfate; panthothenic acids such as calcium panthotenate, D-panthothenyl alcohol, pantothenyl ethyl ether, acetyl panthothenylethyl ether, etc.; vitamin D's such as ergocalcipherol, cholecalcipherol, etc.; nicotinic acids such as nicotinic acid, nicotinic acid amide, nicotinic acid benzyl, etc.; vitamin E's such as α-tocopherol, tocopherol acetate, DL-α-tocopherol nicotinate, DL-α-tocopherol succinate, etc.; vitamins such as vitamin P, biotin, etc.; oily components such as avocado oil, palm oil, peanut oil, tallow, rice bran oil, jojoba oil, evening primrose oil, carunauba wax, lanolin, fluid paraffin, squalane, isosteary palmitate, isostearyl alcohol, glycerine tri-2-ethylhexanoate, etc.; humectants such as glycerine, sorbitol, polyethylene glycol, 1,3-butylene glycol, collagen, hyaluronic acid, condrhoitin sulfate, sodium dextran sulfate, etc.; UV-absorbers such as p-amyl dimethylaminobenzoate, sodium 2-hydroxy-4-methoxybenzophenone- 5-sulfonate, urocanoic acid, ethyl diisopropyl sorbate, etc.; antioxidants such as sodium erisorbate, p-hydroxyanisole, etc.; surfactants such as sodium stearyl sulfate, diethanolamine cetyl sulfate, cetyltrimethyl ammonium saccharine, polyethylene glycol isostearate, glyceryl arachinate, diglycerine diisostearate, phospholipids, etc.; preservatives such as ethyl p-benzoate, butyl p-benzoate, etc.; antiphlogistants such as glycyrrhizinic acid derivatives, salicylic acid derivatives, hynoquintiol, zinc acetate, allantoin, etc.; whiteners such as placenta extracts, glutathione, strawberry geranium extracts, etc.; activators such as extracts of Phellodendron Bank, Coptis Rhizome, Lithospermum Root, peony Japanese green gentian, birch, seige, Japanese medlar, carrot, aloe, mallow iris, grape, Coix seed, dishcloth gourd, lily, safran, Cnidium Rhizome, Ginger, Saint-John's-wort, onions, Rose Mary, garlic, etc., royal jelly, photosensitive material, cholesterol derivatives, young cattle blood extract, etc.; bollod circulators such as γ-oriazanol; antiseborrheics such as sulfur, thiantol, etc.; thickeners such as carboxymethyl cellulose, carboxyhydroxypropyl cellulose, etc.; colorants such as titanium yellow, carsamine, safflower red, etc.; resin powder such as polyethylene, nylon, etc.; perfumes; water; alcohols; and so on.

Further, according to the present invention, an external skin ulcer agent is provided.

Most ulcers caused by decubitus and burns expose the granulation tissue, and bacterial infections are observed accompanied with an increase of oozing fluid, until a systemic infection of septicemia or bacteremia sometimes occurs.

To prevent this, an external skin ulcer agent comprising an absorptive material, which absorbs the oozed fluid from he skin ulcer portion without accumulation, formulated with a pharmaceutical is employed. As such an absorptive material, there have been utilized dextrin and dextran crosslinked products, white sucrose, aluminum hydroxide gel, etc., but all of these must be formulated in large amounts, to sufficiently absorb oozed fluid while maintaining an adequate water content at the skin ulcer.

In contrast, the complex material according to the present invention can sufficiently fulfill these functions in a small amount, and becomes an elastic gel when it absorbs an oozed liquid; thus protecting the skin ulcer portion. Therefore, by a formulation of the present complex material, an external skin ulcer agent not know in the art can be provided. The external skin ulcer agent can be formed into a preparation by conventional method, but if necessary, in addition to the present complex material and the pharmaceutical various additives such as preservatives, colorants, extenders, etc. can be formulated. The amount of the present complex material formulated is not particularly limited, but is desirably 5% by weight or more, to absorb the fluid excreted from within the body. The pharmaceutical to be used in the present invention is not particularly limited, but in addition to sterilizers such as quaternary ammonium salts, iodine, coridone iodine, etc., the above-mentioned granulation formation promotor, various antibiotics and blood circulation promotors, etc. can be formulated. The dosage form also is not particularly limited, but an ointment, cream, lotion, powder spray, etc. are preferred.

EXAMPLES

The present invention is now described in detail with reference to Examples, by which the present invention is no way limited.

Example 1

An aqueous 2% Hibis 104 (Wako Junyaku) solution and an aqueous 2% Laponite XLG dispersion (Laporte) were added so that the weight fractions based on solids of Hibis 104 were 0.2, 0.35, 0.5, 0.65, 0.75, 0.85, 0.95, the mixture was uniformly mixed by a homonixer, and each mixture was adjusted to pH 6.3 with 2N NaOH.

Next, under stirring, a two-fold amount of acetone was added to each mixture to make it turbid, and the mixture was centrifuged at 3000 rpm for 10 minutes, followed by a recovery of the precipitates. The respective recovered precipitates were vacuum dried at 60° C. for 16 hours to obtain various kinds of complex powders (yield: all 90% or more).

For these respective complex materials, to evaluate the gel strength and swelling ability during gelation, the hardness and swelling ratio in pure water were examined. The hardness was measured by dispersing the complex material to 0.5% in pure water, and after swelling sufficiently with water, determining same by a Neocardmeter (M-302 Model, produced by Iio Denki Kogyo). The swelling ratio was measured by sampling 50 mg of the complex material in a commercially available tea bag, and calculating it from the weight gain when it was left to stand in 1000 ml of pure water for about one hour. As Controls, measurements were also conducted for the Hibis (a crosslinked polyacrylic acid) 104 neutralized product, Laponite (a layered silicate mineral) XLG, Aerosol (a swellable particulate silica) #300 and water absorptive resin for paper diapers CA-W4 (Nippon Shokubai). The results are shown in Table 2.

TABLE 2

Hardness and swelling ratio of Hibis 104/Laponite XLG complex

| Hibis 104 weight fraction in complex | Hardness (0.5%) | Swelling ratio (pure water) |
|---|---|---|
| 0.2 | 2 | 104 |
| 0.35 | 5 | 151 |
| 0.5 | 12 | 243 |
| 0.65 | 16 | 347 |
| 0.75 | 20 | 510 |
| 0.85 | 24 | 478 |
| 0.95 | 8 | 450 |
| (Control) | | |
| Hibis Neutralized product | 1 | 353 |
| Laponite XLG | 0 | 106 |
| Aerosol #300 | 0 | 120 |
| CA - W4 | 3 | 287 |

As apparent from Table 2, the complex material of the present invention has an excellent hardness and swelling ratio. Particularly, one with a weight fraction of Hibis 104 exceeding 0.3 is superior.

FIG. 3 shows flow curves of 0.5% gel of the complex material at Hibis 104 weight fraction=0.85 together with flow curves for 1% gel of Hibis 104 neutralized product, and 2% gel of Laponite XLG. It can be seen that the gel of the complex material has the highest yield value and viscosity, although having the lowest concentration.

FIG. 1 shows the infrared absorption spectrum (measured by KBr) of the complex material with a Hibis 104 weight fraction=0.75 obtained in Example 1.

Examples 2 and 3

The preparation method and evaluation method in Example 1 were repeated except for using 2% aqueous carboxymethyl cellulose (Gotoku Yakuhin, TPT-1200) solution and 2% aqueous dispersion of Laponite XLG (Laporte) in place of 2% aqueous Hibis 104 (Wako Junyaku) solution and 2% aqueous dispersion of Laponite XLG (Laporte) and adding carboxymethyl cellulose at weight fractions calculated on solids of 0.1, 0.2, 0.3, 0.4 0.6, 0.7, 0.8 and 0.9, respectively. The Control is the evaluation of the starting material alone.

Figure 2:
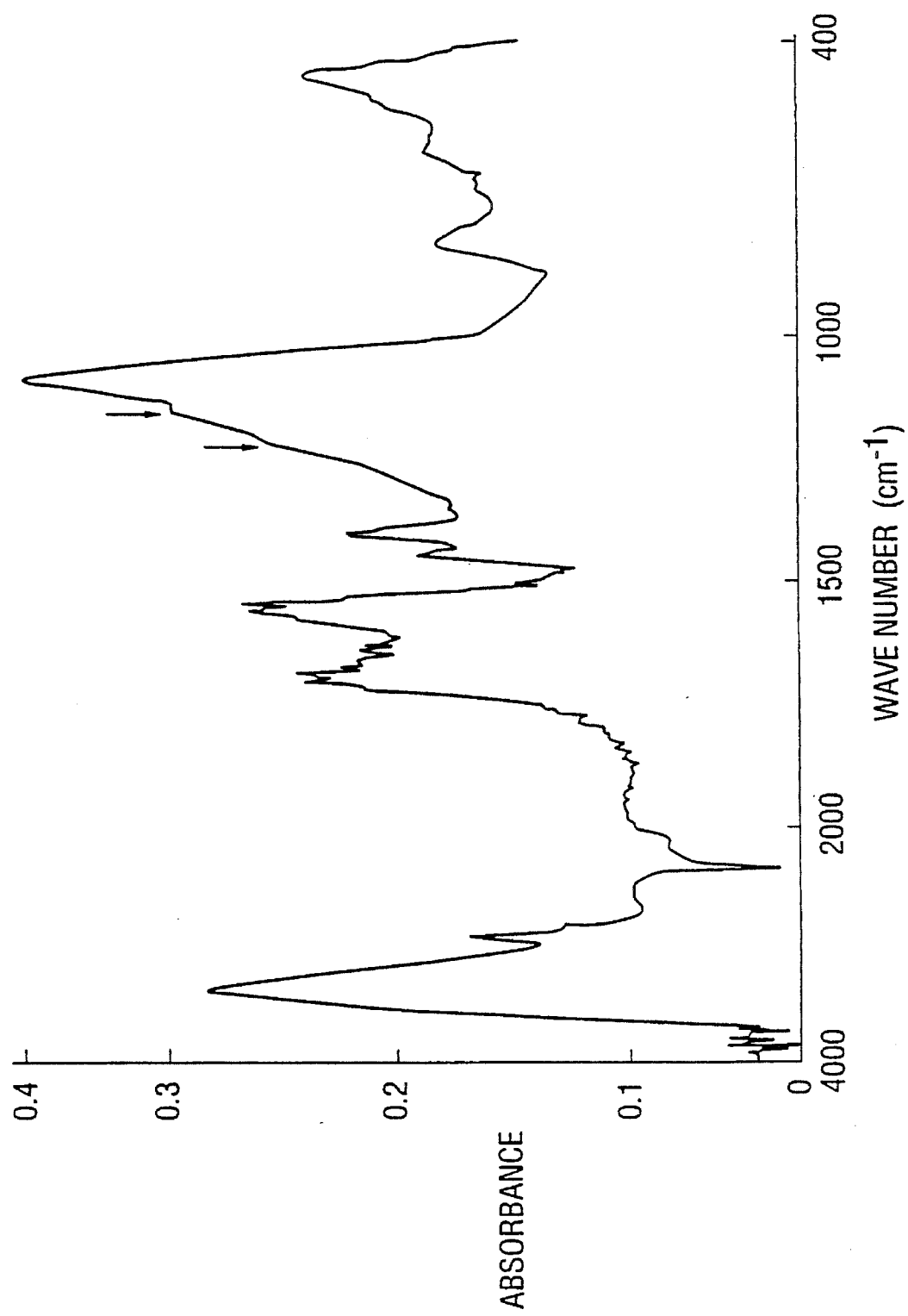
FIG. 2 shows the IR-absorption spectrum of the complex material of the present invention comprising the acrylic acid type polymer and the swellable fine particulate silica of Example 3.

Also, the preparation method and evaluation method in Example 1 were repeated except for using 2% aqueous solution of Hibis 104 (Wako Junyaku) and 2% aqueous dispersion of Aerosil #300 (Nippon Aerosil), and adding Hibit 104 at the weight fractions calculated on solids of 0.2, 0.35, 0.5, 0.65, 0.75, 0.85, 0.95. FIG. 2 shows the FT-IR spectrum of the complex obtained (Hibis 104 weight fraction=0.75). The evaluations results are shown in Table 3 and Table 4, respectively.

TABLE 3

Hardness of TPT-1200/LaDonite XLG complex

| weight fraction of TPT-1200 | Hardness in pure water | in physiological saline |
|---|---|---|
| 0.1 | 2 | 1 |
| 0.2 | 4 | 3 |
| 0.3 | 6 | 4 |
| 0.4 | 2 | 1 |
| 0.6 | 0 | 0 |
| 0.7 | 0 | 0 |
| 0.8 | 2 | 1 |
| 0.9 | 0 | 0 |
| (Control) | | |
| TPT-1200 | 0 | 0 |
| Laponite XLG | 0 | 0 |

TABLE 4

Hardness and swelling ratio of Hibis 104/Aerosil #300 complex

| Hibis 104 weight fraction in complex | Hardness (1.0%) | Swelling ratio (pure water) |
|---|---|---|
| 0.2 | 0 | 102 |
| 0.35 | 0 | 148 |
| 0.5 | 52.5 | 233 |
| 0.65 | 52.4 | 398 |
| 0.75 | 40.3 | 488 |
| 0.85 | 42.4 | 409 |
| 0.90 | 38.0 | 482 |

Viscosity

Figure 4A:
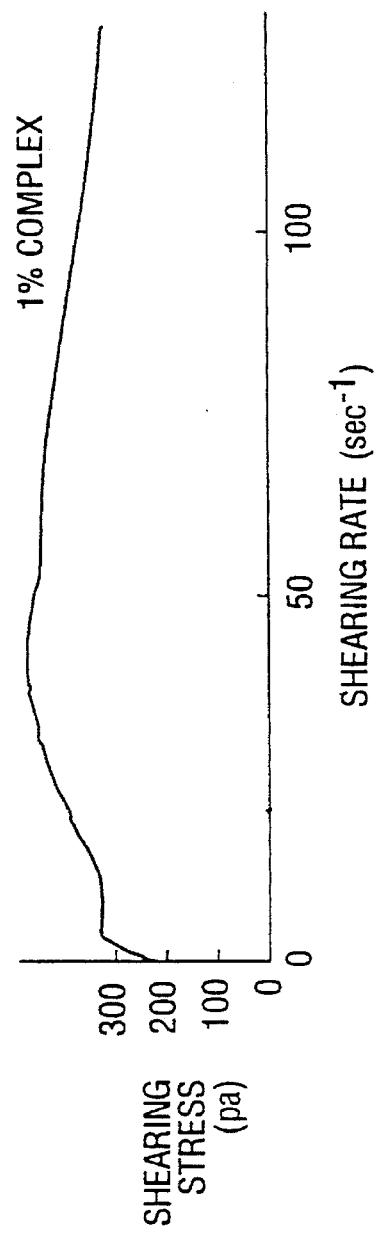
FIG. 4 is a graph showing the flow curve of the 1.0% gel of the complex material of Example 2 (Hibis weight fraction=0.75) together with that of the 1% gel of the Hibis 104 neutralized product.
Figure 4B:
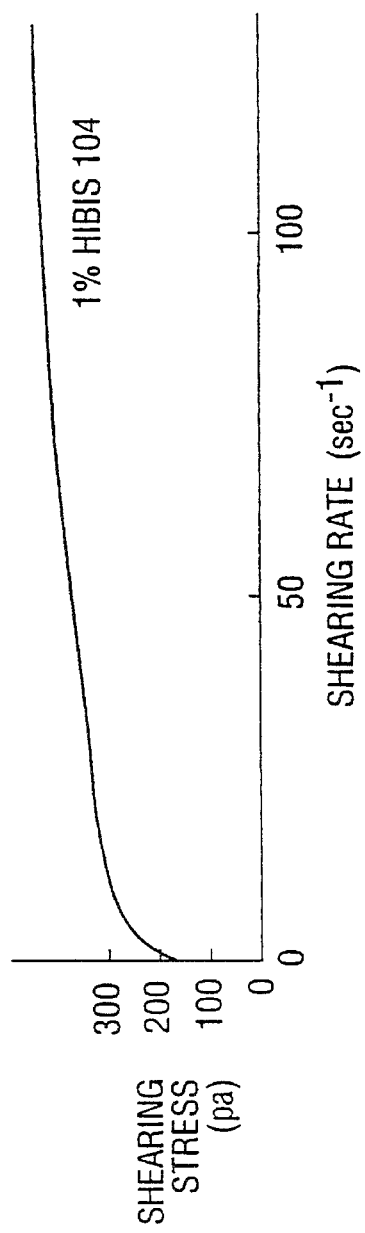

FIG. 4 shows the flow cure of the 1.0% gel of the complex of the present invention (Hibis 104 weight fraction=0.75), together with the flow curve for the 1.0% gel of the Hibis 104 neutralized product.

From FIG. 4, it can be seen that the gel of the complex material has a higher yield value compared with that of Hibis 104, although having a lower concentration.

Comparative Example 1

For an evaluation of the prior art, a preparation of a complex material was attempted with a combination of a straight chain poly(acrylic acid) or a crosslinked poly-(acrylic acid) with magnesium hydroxide, calcium hydroxide, aluminum hydroxide, aluminum sulfate, potash alum, silica gel, or Laponite XLG. More specifically, to 100 ml of a 3% aqueous solution of the former, 100 ml of a 1% aqueous dispersion of the latter was added, and after uniform mixing, the mixture was neutralized with 5% aqueous sodium hydroxide under stirring. An amount 500 ml of acetone was added thereto, followed by recovery of the precipitates by suction precipitation. Next, the precipitates were vacuum dried at 50° C. for 16 hours and optionally crushed in a mortar, to obtain various kinds of complex powders. At the same time, a preparation of the complex material of Emerson was attempted according to the literature. For these complex materials, the hardness and swelling ratio were examined in the same manner as in example 1, to obtain the results shown in Table 5. It can be seen that each system does not have a hardness and swelling ratio as does the complex material according to the present invention.

The complex material using the acidic polysaccharide of the present invention is specific in that the gel strength will be little influenced by salts, although the hardness itself cannot be made too high.

TABLE 5

Evaluation of prior art (Comparative example)

| Combination | Hardness (0.5%) | Swelling ratio (pure water) |
|---|---|---|
| Complex of Emerson | 0 | 84 |
| Hibis 104/Mg(OH)$_2$ | 0 | 211 |
| Hibis 104/Ca(OH)$_2$ | Precipitation agglomeration | |
| Hibis 104/Al(OH)$_3$ | 0 | 218 |
| Hibis 104/Al$_2$(SO$_4$)$_3$ | 0 | 265 |
| Hibis 104/potash alum | 10 | 376 |
| Hibis 104/Silica gel | 12 | 347 |

Example 4

To each 100 ml aqueous 3% solution of straight chain poly(acrylic acids) with average molecular weights of 250,000, 750,000, 1,000,000 and 4,000,000, 100 ml of a 1% aqueous dispersion of Laponite XLG was added, and the mixture was uniformly mixed and then adjusted to pH 6.25 with 5% sodium hydroxide under stirring. To the resultant mixture was added 500 ml of acetone, and the precipitates generated were recovered by suction filtration. Next, the precipitates were vacuum dried at 50° C. for 16 hours, and further optionally crushed in a mortar to obtain various kinds of complex material powder. For these complex materials, the hardness and swelling ratio in pure water were examined in the same manner as in Example 1. The results are shown in Table 6. In the Table, PAA (25), PAA (75), PAA (100), PAA (400) mean poly(acrylic acids) with average molecular weights of 250,000, 750,000, 1,000,000 and 4,000,000, respectively. As the molecular weight of poly(acrylic acid) is larger, both the hardness and swelling ratio become larger, but it can be understood that a complex formation occurs with at least an average molecular weight of 500,000 or higher.

TABLE 6

Complex material of straight chain poly(acrylic acid) and Laponite XLG

| Combination | Hardness (0.5%) | Swelling ratio (pure water) |
|---|---|---|
| PAA(25)/Laponite XLG | separated | |
| PAA(75)/Laponite XLG$_2$ | 4 | 350 |
| PAA(100)/Laponite XLG | 10 | 348 |
| PAA(400)/Laponite XLG | 13 | 422 |

Example 5

To 500 ml of an aqueous 3% Carbopol 934 (Goodrich), each 500 ml aqueous 1% dispersion of various Smectite species layered silicate minerals of Kunipia (Kunimine Kogyo), Beagam (Vanderbilt), Smectone SA (Kunimine Kogyo), or Laponite XLG, and after uniform mixing, 25 g of anhydrous sodium acetate was added, followed by adjustment to pH 6.4 with 10% sodium hydroxide under well stirring. Next, to the mixture, was added 1500 ml of methanol and the precipitates emerged were separated and collected by suction filtration. The precipitates were further washed with methanol twice for a removal of the remaining sodium acetate, and then vacuum dried at room temperature for about 20 hours to obtain 18.9 g of a complex material powder. For these respective complex materials, the hardness and swelling ratio in pure water were measured in the same manner as in Example 1. The results are as shown in Table 7, and it can be seen that they have a hardness and swelling ratio equal to those of the complex material of Example 1.

TABLE 7

Hardness and swelling ratio of Carbopol 934/Smectite type silicate mineral complex material

| Water-swellable silicate mineral name | Hardness (0.5%) | Swelling ratio (pure water) |
|---|---|---|
| Kunipia | 19 | 485 |
| Beagam | 20 | 496 |
| Smectone SA | 21 | 546 |
| Laponite XLG | 20 | 510 |

Example 6

According to the same procedure as described in Example 5, 500 ml of an aqueous 3% Carbopol 934 solution was mixed uniformly with each 500 ml of an 1% aqueous dispersion of Kunipia, Beagam, Smectone SA or Laponite XLG, and each mixture was adjusted to pH 6.0 with 10% sodium hydroxide under stirring. Each mixture was spray dried as such to obtain dry fine powder of complex material, and hardness and swelling ratio in pure water were measured. The results are shown in Table 8. From the results, it can be seen that a complex material having properties equal to those in Example 5 can be obtained without the use of an organic solvent.

TABLE 8

Hardness and swelling ratio of Carbopol 934/Smectite type silicate mineral complex material prepared by spray drying

| Water-swellable silicate mineral name | Hardness (0.5%) | Swelling ratio (pure water) |
|---|---|---|
| Kunipia | 20 | 492 |
| Beagam | 20 | 486 |
| Smectone SA | 21 | 509 |
| Laponite XLG | 210 | 518 |

Example 7

After 100 ml of an aqueous 4% Hibis 103 solution and 100 ml of an aqueous 1% vermiculite or chamosite solution were uniformly mixed respectively, the mixture was adjusted to pH 6.3 with addition of 5% potassium hydroxide under stirring. To the mixture was added 300 ml of isopropanol to precipitate the precipitates of the complex material, which were left to stand for one day and night. The supernatant was discarded to recover the precipitates, which were placed in a heated dryer of 120° C. for 6 hours to obtain complex material powders. The hardness and swelling ratio in pure water were measure according to the same procedure as in Example 1, and the results are shown in Table 9.

TABLE 9

Complex material with vermiculite and chamosite

| Combination | Hardness (0.5%) | Swelling ratio (pure water) |
|---|---|---|
| Hibis 103/Vermiculite | 19 | 471 |
| Hibis 103/Chamosite | 18 | 453 |

Example 8

Each of 0.3 g of the complex material prepared in Example 1 with Hibis 104 weight fraction=0.85, 3.5 g of Laponite XLG and 1.2 g of neutralized and dried product of Hibis 104 was dispersed in 100 ml of a 10 mM phosphate buffer of pH 4 and 8, and the gel obtained was left to stand in a sealed system in a thermostatic tank of 50° C. for two months. The states of the gels after two months are summarized in Table 10. It can be seen that the complex material of the present invention has an excellent thermal stability.

TABLE 10

Stability of complex material

| Sample | Stability (pH 4) | Stability (pH 8) |
|---|---|---|
| Complex material | Stable | Stable |
| Laponite XLG | Precipitated | Stable |
| Hibis 104 neutralized product | Slight water liberation | Stable |

Example 9

A 1% aqueous solution of Hibis 104 and a 1% aqueous solution of Laponite XLG were mixed at 3:1 by weight, and then divided into 9 aliquots, which were respectively adjusted from pH 4 to 10 with 10% sodium hydroxide. At this time, the gels of various pH were subjected to a measurement of the hardness thereof, and then 2-fold amount of acetone was added to each gel to recover the complex material as precipitates, which were vacuum dried at 60° C. to obtain a complex material powder. This powder was again dispersed to 1% in pure water, and the hardness measured. The results are shown in Table 11. It can be understood that the gel has a maximum value at a pH of 5 to 7, particularly at 6.0 to 6.5, both before and after drying. Further, it can be alos understood that the hardness is increased to about two-fold by drying.

TABLE 11

Gel hardness dependency on pH and influence by drying

| pH before drying | hardness before drying (1%) | hardness after drying (1%) |
|---|---|---|
| 4.3 | 9 | 17 |
| 5.0 | 18 | 34 |
| 5.4 | 23 | 42 |
| 6.0 | 27 | 50 |
| 6.3 | 29 | 51 |
| 6.6 | 26 | 49 |
| 7.1 | 23 | 45 |
| 8.6 | 22 | 45 |
| 9.8 | 21 | 44 |

Example 10

Swelling rate of the complex material prepared from the gel of pH 6.3 in Example 9 and a water absorptive polymer presently used for paper diapers (Nippon Shokubai, CA-W4) relative to pure water were examined. For the test method, there was employed a simple method of suspending a defatted cotton in pure water in a laboratory dish, and setting a nonwaven fabric having a test substance mounted thereon. The swelling rate was examined by the change of the weight of the test substance with a lapse of time. The results are summarized in Table 12. It can be understood that both have a substantially equal swelling rate.

TABLE 12

Swelling rate

| | Swelling ratio | |
|---|---|---|
| Time (min.) | Complex material | CA - W4 |
| 0 | 1 | 1 |
| 3 | 1 | 1 |
| 6 | 8 | 9 |
| 10 | 25 | 20 |
| 15 | 155 | 160 |
| 60 | 290 | 270 |
| 120 | 350 | 330 |

Example 11

The complex material prepared by drying from the gel of pH 6.3 in Example 9 was placed in McIlvain buffer of pH 1 to 8, Liquid 1 (artificial gastric juice) and Liquid 2 (artificial enteric juice) listed in Japanese Pharmacopoeia sampled in a measuring cylinder for an examination of equilibrated value of swelling ratio. In this case, the swelling ratio was read from the graduation on the measuring cylinder. The results were summarized in Table 13. It can be clearly seen that the swelling ratio depends strongly on the pH.

TABLE 13

Swelling ratio dependency on pH

| pH | Swelling ratio |
|---|---|
| 2.2 | 8 |
| 2.6 | 12 |
| 3.0 | 22 |
| 3.4 | 36 |
| 3.8 | 48 |
| 4.2 | 62 |
| 4.6 | 76 |
| 5.0 | 80 |
| 5.4 | 80 |
| 5.8 | 81 |
| 7.0 | 82 |
| 8.0 | 80 |
| Artificial gastric juice (1.2) | 9 |
| Artificial enteric juice (6.8) | 120 |

Example 12

The preparation method and evaluation method in Example 1 were repeated except for using 2% aqueous solution of a poly(methacrylic acid) (General Science) and a 2% aqueous dispersion of Laponite XLG (Laporte) as the starting materials, Results similar to those of Table 2 are shown in Table 14.

TABLE 14

Hardness and swelling ratio of poly(methacrylic acid) Laconite-XLG complex material

| Poly(methacrylic acid) weight fraction in complex material | Hardness (0.5%) | Swelling ratio (pure water) |
|---|---|---|
| 0.2 | 1 | 100 |
| 0.35 | 4 | 145 |
| 0.5 | 10 | 236 |
| 0.65 | 14 | 338 |
| 0.75 | 19 | 492 |
| 0.85 | 22 | 469 |
| 0.95 | 6 | 431 |
| Laponite XLG | 0 | 106 |
| CA - W4 | 3 | 287 |

As apparent from Table 14, the complex material of the present invention has an excellent hardness and swelling ratio. Particularly, it can be appreciated that on with a weight fraction of poly(methacrylic acid) exceeding 0.3 is superior.

Example 13

Example 4 was repeated except for using a poly(methacrylic acid) having a similar average molecular weight in place of the poly(acrylic acid).

For the complex materials thus obtained, as in Example 12, the hardness and swelling ratio in pure water were examined. The results are shown in Table 15. In the Table, PMAA (25), PMAA (75), PMAA (100), PMAA (400) mean poly(methacrylic acids) with average molecular weights of 250,000, 750,000, 1,000,000 and 4,000,000, respectively. It can be seen that the hardness and swelling ratio will be greater as the molecular weight of poly(methacrylic acid) is larger, but a complex formation can be effected with at least an average molecular weight of 500,000 or more.

TABLE 15

Complex material of straight chain poly(methacrylic acid) and Laponite XLG

| Combination | Hardness (0.5%) | Swelling ratio (pure water) |
|---|---|---|
| PmAA(25)/Laponite XLG | separated | |
| PmAA(75)/Laponite XLG | 10 | 368 |
| PmAA(100)/Laponite XLG | 17 | 418 |
| PmAA(400)/Laponite XLG | 19 | 486 |

Example 14

Example 5 was repeated except for using a poly(methacrylic acid) (General Science) in place of using Carbopol 934 (Goodrich) as the starting material, and using a 10% sodium hydroxide of pH 6.4 in place of that of a pH of 6.3 for a pH adjustment of the uniform mixture. The results are shown in Table 16.

TABLE 16

Hardness and swelling ratio of poly(methacrylic acid) Smectite type silicate mineral complex material

| Water-swellable silicate mineral | Hardness (0.5%) | Swelling ratio (pure water) |
|---|---|---|
| Kunipia | 16 | 455 |

TABLE 16-continued

Hardness and swelling ratio of poly(methacrylic acid) Smectite type silicate mineral complex material

| Water-swellable silicate mineral | Hardness (0.5%) | Swelling ratio (pure water) |
|---|---|---|
| Beagam | 19 | 466 |
| Smectone SA | 20 | 464 |
| Laponite XLG | 19 | 500 |

Example 15

According to the same procedure as described in Example 14, 500 ml of an aqueous 3% poly(methacrylic acid) (General Science) solution was mixed uniformly with each 500 ml of an 1% aqueous dispersion of Kunipia, Beagam, Smectone SA or Laponite XLG, and each mixture was adjusted to pH 6.3 with 10% sodium hydroxide under stirring. Each mixture was spray dried as such to obtain dry fine powder of complex material, and hardness and swelling ratio in pure water were measured. The results are shown in Table 17. From these results, it can be seen that a complex material having properties equal to those in Example 14 can be obtained without the use of an organic solvent.

TABLE 17

Hardness and swelling ratio of poly(methacrylic acid)/ Smectite type silicate mineral complex material prepared by spray drying

| Water-swellable silicate mineral | Hardness (0.5%) | Swelling ratio (pure water) |
|---|---|---|
| Kunipia | 17 | 462 |
| Beagam | 19 | 466 |
| Smectone SA | 19 | 480 |
| Laponite XLG | 20 | 488 |

Example 16

A 1% aqueous solution of a poly(methacrylic acid) and a 1% aqueous solution of Laponite XLG were mixed at 3:1 by weight, and then divided into 9 aliquots, which were respectively adjusted from pH 4 to 9 with 10% sodium hydroxide. At this time, the gels of various pH were subjected to a measurement of the hardness thereof, and then 2-fold amount of acetone was added to each gel to recover the complex material as the precipitates, which were vacuum dried at 60° C. to obtain complex material powders.

These powders were again dispersed to 1% in pure water, and the hardnesses were measured. The results are shown in Table 18. It can be understood that the gel has the maximum value at a pH of 5 to 7, particularly at 6.0 to 6.5, both before and after drying. Further, it can be also understood that the hardness is increased to about two-fold by drying.

TABLE 18

Gel hardness dependency on pH and influence by drying

| pH before drying | hardness before drying (1%) | hardness after drying (1%) |
|---|---|---|
| 4.3 | 9 | 15 |
| 5.0 | 17 | 33 |
| 5.4 | 21 | 40 |
| 6.0 | 25 | 47 |

TABLE 18-continued

Gel hardness dependency on pH and influence by drying

| pH before drying | hardness before drying (1%) | hardness after drying (1%) |
|---|---|---|
| 6.3 | 28 | 50 |
| 6.6 | 24 | 46 |
| 7.1 | 22 | 43 |
| 8.6 | 20 | 41 |
| 9.8 | 18 | 38 |

Example 17

The tests were conducted in the same manner as in Example 10 except for using the complex prepared by drying from the gel having a pH of 6.3 in Example 16.

The results are shown in Table 19. It can be understood that the water absorptive polymer CA-W4 of the prior art (Nippon Shokubai) and the complex of the present invention have an equal swelling rate.

TABLE 19

Swelling rate

| | Swelling ratio | |
|---|---|---|
| Time (min.) | Complex material | CA-W4 |
| 0 | 1 | 1 |
| 3 | 1 | 1 |
| 6 | 8 | 9 |
| 10 | 24 | 20 |
| 15 | 151 | 160 |
| 60 | 270 | 270 |
| 120 | 340 | 330 |

(Preparation and evaluation of gel-like aromatic compositions)

Example 18

Preparation of Complex Material—1

To a 2% aqueous solution of a poly(acrylic acid) with a molecular weight of about 4,000,000 (Alrdich), was added either one of 2% aqueous solution of Laponite XLG (Laporte), Kunipia, Smectone SA (all produced by Kunimine Kogyo), Beagam (Vanderbilt) which are water-swellable silicate mineral, to a weight fraction calculated on solids of the poly(acrylic acid) of 0.75, and after uniformly mixed by a homomixer, each mixture was adjusted to a pH of 6.3 with 2N NaOH. Next, under stirring, 2-fold amount of ethanol was added to each mixture, and the precipitates of the complex material powder were recovered. The respective precipitates recovered were vacuum dried at 60° C. for 16 hours to obtain powders of various complex materials (yields were all 90% or higher). By using the complex materials obtained, the gel-like aromatic compositions shown below were prepared.

Preparation of Complex Material—2

The method of the Preparation of complex material—1 was repeated except for using Aerosil #200, #300, #380 as the above-mentioned water swellable silicate mineral.

Preparation of Complex Material—3

A 2% aqueous solution of carboxymethyl cellulose (Gotoku Yakuhin, TPT-1200) was first ion exchanged with Amberlite IR-120B (Organo), and then either one of Laponite XLG (Laporte), Kunipia (Kunimine Kogyo), Beagam (Vanderbilt), Smectone SA (Kunimina Kogyo), bentonite of Japanese Pharmacopoeia as a water-swellable silicate mineral was added to a weight fraction calculated on solids of carboxymethyl cellulose of 0.75. The mixture uniformly mixed by a homomixer, and each mixture adjusted to a pH of 6.3 with 2N NaOH. Next, under stirring, a 2-fold amount of ethanol was added to each mixture to recover the complex by precipitation. The respective precipitates recovered were vacuum dried at 60° C. for 16 hours, to obtain various kinds of complex powders (yields were all 90% or higher).

Using the complex materials obtained as described above, the gel-like aromatic compositions shown below were prepared.

Example 19

After the antioxidant and the colorant were dissolved in the perfume, each solution was dispersed in the respective complex material gels swelled with deionized water and sealed.

| Perfume | 31.6 |
|---|---|
| Antioxidant | 0.3 |
| Colorant | q.s. |
| Complex material* | 1.5 |
| Deionized water | 66.6 |

[*poly(acrylic acid)/Laponite complex material (corresponding product: PAL-1), poly(acrylic acid)/Aerosil #300 complex material (corresponding product: PAE3-2) or carboxymethyl cellulose/Laponite complex (corresponding product: CML-3)].

Example 20

A solution of Theodor, a perfume, an antioxidant, a colorant dissolved in ethyl alcohol heated to 40° C. was left to cool to room temperature, and then dispersed into a complex material gel swelled with deionized water and sealed.

| Perfume | 3.2 |
|---|---|
| Ethyl alcohol | 0.6 |
| Theodor E-2020 (Nippon Emulsion) | 2.5 |
| Antioxidant | 0.1 |
| Colorant | q.s. |
| Complex material* | 2.0 |
| Deionized water | 91.6 |

[*poly(acrylic acid)/Kunipia complex material (corresponding product: PAK-1), poly(acrylic acid)/Aerosil #200 complex material (corresponding product: PAE2-2) or carboxymethyl cellulose/Kunipia complex (corresponding product: CMK-3)].

Example 21

Example 20 was repeated except that the same components as in Example 20 were formulated according to the following composition.

| Perfume | 4.8 |
|---|---|
| Ethyl alcohol | 16.8 |
| Theodor E-2020 (Nippon Emulsion) | 2.5 |
| Antioxidant | 0.1 |
| Colorant | q.s. |

-continued

| Complex material* | 0.5 |
|---|---|
| Deionized water | 75.3 |

[*poly(acrylic acid)/Kunipia complex material (corresponding product: PAK-11), poly(acrylic acid)/Aerosil #200 complex material (corresponding product: PAE2-22) or carboxymethyl cellulose/Beagam complex (corresponding product: CMB-3)].

Example 22

A solution of Theodor, a perfume, an antioxidant, a colorant dissolved in 3-methyl-3-methoxybutanol heated to 40° C. was left to cool to room temperature, and then dispersed into a complex material gel swelled with deionized water and sealed.

| Perfume | 3.2 |
|---|---|
| 3-Methyl-3-methoxybutanol | 42.4 |
| Theodor E-2020 | 5.0 |
| Antioxidant | 0.1 |
| Colorant | q.s. |
| Complex material* | 0.4 |
| Deionized water | 49.6 |

[*poly(acrylic acid)/Smectone complex material (corresponding product: PAS-1), poly(acrylic acid)/Aerosil #300 complex material (corresponding product: PAE3-22) or carboxymethyl cellulose/Smectone complex (Corresponding product: CMS-3).

Example 23

A solution of Tween 60, a perfume, an antioxidant, a colorant dissolved in ethyl alcohol and 3-methyl- 3-methoxybutanol heated to 40° C. was left to cool to room temperature, and then dispersed into a complex material gel swelled with deionized water and sealed.

| Perfume | 1.0 |
|---|---|
| Ethyl alcohol | 20.0 |
| 3-Methyl-3-methoxybutanol | 38.8 |
| Tween 60 (Nikko Chemicals) | 6.5 |
| Antioxidant | 0.1 |
| Colorant | q.s. |
| Complex material* | 1.0 |
| Deionized water | 32.6 |

[*poly(acrylic acid)/Smectone complex material (corresponding product: PAS-11), poly(acrylic acid)/Aerosil #300 complex material (corresponding product: PAE3-222) or carboxymethyl cellulose/Laponite complex (corresponding product: CML-33)].

Comparative Example 2

Agar was added to deionized water and heated at to 100° C. to be dissolved therein, and to the resultant solution were added Tween 60, a perfume and methyl p-benzoate at 50° to 60° C. An amount of 50 g of the mixture was charged into a vessel, left to cool at room temperature and then sealed.

| Agar | 1.7 |
|---|---|
| Propylene glycol | 5.0 |
| Methyl p-benzoate | 0.2 |
| Tween 60 (Nikko Chemicals) | 1.5 |
| Perfume | 5.0 |
| Deionized water | 86.6 |

Comparative Example 3

Carrageenan was added into deionized water and heated at 60° to 70° C. to be dissolved therein, and to the resultant solution were added Tween 60, a perfume and methyl p-benzoate at 50° to 60° C. An amount of 50 g of the mixture was charged into a vessel, left to cool at room temperature and then sealed.

| Carrageenan | 3.5 |
|---|---|
| Propylene glycol | 3.0 |
| Methyl p-benzoate | 0.2 |
| Tween 60 (Nippon Chemicals) | 1.5 |
| Perfume | 5.0 |
| Deionized water | 86.6 |

Comparative Example 4

Silica gel was added to a perfume, and the mixture was dispersed in a water absorptive polymer gel swelled with deionized water and sealed.

| Perfume | 1.0 |
|---|---|
| Silica gel (Shionogi Seiyaku) | 0.5 |
| Water absorptive polymer | 0.5 |
| (Balgus 500B produced by Taiyo Kagaku) | |
| Deionized water | 98.0 |

Evaluation

For the gel-like aromatic compositions prepared in Comparative Example 2 to 4, and Examples 19 to 23, the stability as described below was examined.
(a) Stability of Perfume During Storage The respective gel-like aromatic compositions were left at −5° to 40° C. for one month, and an evaluation of the smell by a panel of experts was made organoleptically, according to the standards shown below.

1: no change at all
2: very slight change
3: slight change
4: some change
5: clear change (b) Stability of Contents During Storage The respective gel-like aromatic compositions were left to stand at −5° to 40° C. for one month, and the change in appearance, particularly water liberation was observed. Judgements were conducted in the same manner as for the above item (a). The results of (a) and (b) are shown in Table 20.

TABLE 20

| | Evaluation results of stability of perfume | | | | | |
|---|---|---|---|---|---|---|
| | Stability (a) | | | | | |
| Panel | A | B | C | D | E | Stability (b) |
| (Comparative) | | | | | | |
| Example 2 | 2 | 3 | 2 | 2 | 3 | 4 |
| Example 3 | 4 | 4 | 3 | 4 | 5 | 4 |
| Example 4 | 3 | 4 | 3 | 3 | 4 | 1 |
| (Present invention) | | | | | | |
| PAL-1 | 1 | 1 | 1 | 1 | 2 | 1 |
| PAE3-2 | 1 | 1 | 1 | 1 | 2 | 1 |
| CML-3 | 1 | 1 | 1 | 1 | 2 | 1 |
| PAK-1 | 2 | 2 | 1 | 1 | 2 | 1 |
| PAE2-2 | 2 | 2 | 1 | 1 | 2 | 1 |
| CMK-3 | 2 | 2 | 1 | 1 | 2 | 1 |
| PAK-11 | 2 | 1 | 1 | 1 | 2 | 1 |
| PAE2-22 | 2 | 1 | 1 | 1 | 2 | 1 |

TABLE 20-continued

Evaluation results of stability of perfume

| Panel | Stability (a) | | | | | Stability (b) |
| --- | --- | --- | --- | --- | --- | --- |
| | A | B | C | D | E | |
| CMB-3 | 2 | 1 | 1 | 1 | 2 | 1 |
| PAS-1 | 3 | 2 | 2 | 2 | 1 | 1 |
| PAE3-22 | 3 | 2 | 2 | 2 | 1 | 1 |
| CMS-3 | 3 | 2 | 2 | 2 | 1 | 1 |
| PAS-11 | 2 | 1 | 1 | 2 | 2 | 1 |
| PAE3-222 | 2 | 1 | 1 | 2 | 2 | 1 |
| CML-33 | 2 | 1 | 1 | 2 | 2 | 1 |

(c) Smell Rise-up and Change of Surface State with Lapse of Time

The respective gel-like aromatic compositions were opened, left to stand at room temperature of 22° to 25° C., and 2 weeks later and one month later, the smell from the gel and its surface state were observed. The judgement of the surface state was conducted in the same manner as for the above item (A), but judgement of the smell was made according to the evaluation standards shown below. The results were as shown in Table 21.

1. very strong smell
2. slightly strong smell
3. usual smell
4. slightly weak smell
5. very weak smell

TABLE 21

Evaluation results of smell rise-up and surface state

| | Smell | | Surface state | |
| --- | --- | --- | --- | --- |
| | 2 weeks | 1 month | 2 weeks | 1 month |
| (Comparative) | | | | |
| Example 2 | 2 | 5 | 4 | 5 |
| Example 3 | 2 | 5 | 4 | 5 |
| Example 4 | 4 | 5 | 1 | 2 |
| (Present invention) | | | | |
| PAL-1 | 1 | 1 | 1 | 2 |
| PAE3-2 | 1 | 1 | 1 | 2 |
| CML-3 | 1 | 2 | 1 | 2 |
| PAK-1 | 2 | 2 | 1 | 2 |
| PAE2-2 | 2 | 2 | 1 | 2 |
| CMK-3 | 2 | 3 | 1 | 2 |
| PAK-11 | 2 | 2 | 1 | 2 |
| PAE2-22 | 2 | 2 | 1 | 2 |
| CMB-3 | 2 | 3 | 1 | 2 |
| PAS-1 | 2 | 2 | 1 | 2 |
| PAE3-22 | 2 | 2 | 1 | 2 |
| CMS-3 | 2 | 2 | 1 | 2 |
| PAS-11 | 2 | 3 | 1 | 2 |
| PAE3-222 | 2 | 3 | 1 | 2 |
| CML-33 | 2 | 3 | 1 | 2 |

(Preparation and evaluation of cosmetics)

Example 24

Preparation of Complex Material—11

To a 2% aqueous solution of Hibis 104 as the polyacrylic acid, was added either one of a 2% aqueous solution of Laponite XLG, Kunipia, Smectone SA or Beagam as a water swellable silicate mineral to a weight fraction calculated on solids of Hibis 104 of 0.75, and after uniformly mixed by a homomixer, 2N NaOH was added to each mixture to adjust pH to 6.3. Next, under stirring, 2-fold amount of ethanol was added, and the powder of the complex material was recovered. Each of the precipitates recovered was vacuum dried at 60° C. for 16 hours, to obtain various kinds of complex material powders (yields were all 90% or more).

Preparation of Complex Material—22

Various complex material powders were obtained in the same manner as in Preparation of complex material—2 in Example 18.

Using the complex materials obtained, the following cosmetics were prepared.

Example 25 Nutritious Cream

The oil phase portion A and the aqueous phase portion B shown below were respectively dissolved by heating, the oil phase portion was mixed into the aqueous phase portion, and the mixture was emulsified by an emulsifier. Next, the emulsion was cooled to the final temperature of 30° to obtain a cream. In the following, the amounts formulated are all % by weight.

| (A) Cetanol | 2 |
| --- | --- |
| Stearic acid | 2 |
| Petrolatum | 6 |
| Squalane | 8 |
| Fluid paraffin | 4 |
| Isopropyl myristate | 2 |
| Glyceryl monostearate | 3 |
| Ethyl p-benzoate | 0.2 |
| Perfume | 0.1 |
| (B) Propylene glycol | 2 |
| Glycerine | 5 |
| Complex material* | 0.3 |
| Purified water | 64.3 |
| Potassium hydroxide | 0.1 |
| Talc | 1 |

[*Hibis/Laponite complex material (corresponding product: C-HL-1), Hibis/Aerosil #300 complex material (corresponding product: C-HE3-2)]

Comparative Example 5 Nutritious Cream

A nutritious cream was obtained as in Example 25.

| (A) Cetanol | 2 |
| --- | --- |
| Stearic acid | 2 |
| Petrolatum | 6 |
| Squalane | 8 |
| Fluid paraffin | 4 |
| Isopropyl myristate | 2 |
| Glyceryl monostearate | 3 |
| Ethyl p-benzoate | 0.2 |
| Perfume | 0.1 |
| Glycerine | 5 |
| Hibis 104 | 0.3 |
| Purified water | 64.1 |
| Potassium hydroxide | 0.3 |
| Talc | 1 |

Example 26 Cleaning cream

A Cleansing cream was prepared as in Example 25.

| (A) Nylon powder | 3 |
| --- | --- |
| Beeswax | 1 |
| Solid paraffin | 1 |
| Stearic acid | 2 |

| | | |
|---|---|---|
| | Petrolatum | 10 |
| | Fluid paraffin | 35 |
| | POE(2) monosorbitane monostearate | 2.4 |
| | Diglycerine distearate | 2.6 |
| | Propyl p-benzoate | 0.3 |
| | Perfume | 0.3 |
| (B) | Atherocollagen (Koken) | 1.5 |
| | Complex material* | 0.2 |
| | Dipropylene glycol | 5 |
| | Purified water | 33.55 |
| | Potassium hydroxide | 0.08 |

[*Hibis/Kunipia complex material (corresponding product: C-HK-1), Hibis/Aerosil #380 complex material (corresponding product: C-HE3-22)]

Example 27 Nutritious Milky Lotion

A nutritious milky lotion was prepared as in Example 25.

| | | |
|---|---|---|
| (A) | Polyethylene powder | 2 |
| | Beeswax | 1 |
| | Petrolatum | 2 |
| | Deodorized lanolin | 1.5 |
| | Jojoba oil | 6 |
| | Cetyl isooctanoate | 4 |
| | POE(20)-2-octyldodecanol | 2 |
| | Ethyl p-benzoate | 0.2 |
| | Butyl p-benzoate | 0.1 |
| | Perfume | 0.3 |
| (B) | Sodium hyarulonate | 0.2 |
| | Complex material* | 0.3 |
| | Dipropylene glycol | 2 |
| | Purified water | 78.2 |
| | L-arginine | 0.2 |

[*Hibis/Kunipia complex material (corresponding product: C-HK-1), Hibis/Aerosil #200 complex material (corresponding product: N-HE2-2)]

Example 28 Foundation

A foundation was prepared as in Example 25.

| | | |
|---|---|---|
| (A) | Cetanol | 3.5 |
| | Stearic acid | 2 |
| | Deodorized lanolin | 5 |
| | Petrolatum | 2 |
| | Squalane | 8 |
| | Glyceryl monooleate | 2.5 |
| | POE(10) behenyl alcohol | 0.5 |
| | Ethyl p-benzoate | 0.2 |
| | Butyl p-benzoate | 0.2 |
| (B) | Complex material* | 1 |
| | 1,3-Butylene glycol | 2 |
| | Kaolin | 5 |
| | Talc | 5 |
| | Titanium oxide | 5 |
| | Oxide yellow | 2 |
| | Iron oxide black | 1 |
| | Iron oxide red | 1 |
| | Purified water | 53.85 |
| | Triethanolamine | 0.25 |

[*Hibis/Beagam complex material (corresponding product: F-HB-1), Hibis/Aerosil #300 complex material (corresponding product: F-HE3-2)]

Example 29 Lotion

After the aqueous phase portion A and the alcoholic portion B shown below were uniformly dissolved, respectively, B was added to A to obtain a lotion.

| | | |
|---|---|---|
| (A) | Purified water | 77.64 |
| | Glycerine | 3 |
| | 1,3-Butylene glycol | 10 |
| | Titanium oxide | 1 |
| | Complex material* | 0.2 |
| | Sodium hyarulonate | 0.01 |
| (B) | Ethanol | 7 |
| | POE(60) hardened castor oil | 1 |
| | Perfume | 0.05 |
| | Methyl p-benzoate | 0.1 |

[*Hibis/Smectone complex material (corresponding product: W-HS-1), Hibis/Aerosil #300 complex material (corresponding product: C-HE3-2)]

Example 30 Aqueous Essence

An aqueous essence was prepared as in Example 29.

| | | |
|---|---|---|
| (A) | Purified water | 68.85 |
| | 1,3-Butylene glycol | 6 |
| | Glycerine | 4 |
| | Maltitol | 2 |
| | Complex material* | 0.3 |
| | Hibis/Kunipia complex material | 0.3 |
| | Dipropylene glycol | 5 |
| | Talc | 7 |
| (B) | Ethanol | 5 |
| | POE(60) hardened castor oil | 1 |
| | Vitamin E acetate | 0.1 |
| | Perfume | 0.05 |
| | Oleyl alcohol | 0.2 |
| | Methyl p-benzoate | 0.2 |

[*Hibis/Laponite complex material (corresponding product: A-HL-1), Hibis/Aerosil #380 complex material (corresponding product: A-HE3-2)]

Example 31 Lotion

The aqueous phase portion A and the alcoholic portion B shown below were uniformly dissolved, respectively, and then B was added to A to be mixed and solubilized, followed by an addition of L-arginine C to prepare a lotion.

| | | |
|---|---|---|
| (A) | Purified water | 63.05 |
| | 1,3-Butylene glycol | 10 |
| | Maltitol | 2 |
| | Complex material* | 0.2 |
| | Atherocollagen | 0.05 |
| | Crystalline cellulose | 1 |
| (B) | Ethanol | 20 |
| | 2-Ethylhexyl-p-dimethylaminobenzoate | 1 |
| | Methyl p-benzoate | 0.1 |
| | POE(60) hardened castor oil | 1.2 |
| | Trisodium edetate | 1.2 |
| | Perfume | 0.05 |
| (C) | L-arginine | 0.15 |

[*Hibis/Laponite complex material (corresponding product: D-HL-1), Hibis/Aerosil #300 complex material (corresponding product: D-HE3-2)]

Comparative Example 6 Nutritious Milky Lotion

A nutritious milky lotion was prepared as in Example 25.

| | | |
|---|---|---|
| (A) | Polyethylene powder | 2 |
| | Beeswax | 1 |
| | Petrolatum | 2 |
| | Deodorized lanolin | 1.5 |
| | Jojoba oil | 6 |
| | Cetyl isooctanoate | 4 |
| | POE(20)-2-octyldodecanol | 2 |
| | Ethyl p-benzoate | 0.2 |
| | Butyl p-benzoate | 0.1 |
| | Perfume | 0.3 |
| (B) | Sodium hyarulonate | 0.2 |
| | Hibis 104 | 0.2 |
| | Dipropylene glycol | 2 |

|   |   |
|---|---|
| Purified water | 78.2 |
| L-arginine | 0.2 |
| Sodium hydroxide | 0.1 |

Comparative Example 7 Lotion

A lotion was prepared as in Example 29.

|   |   |   |
|---|---|---|
| (A) | Purified water | 77.52 |
|   | Glycerine | 3 |
|   | 1,3-Butylene glycol | 10 |
|   | Titanium oxide | 1 |
|   | Hibis 103 | 0.2 |
|   | Sodium hyarulonate | 0.03 |
|   | Sodium hydroxide | 0.1 |
| (B) | Ethanol | 7 |
|   | POE(60) hardened castor oil | 1 |
|   | Perfume | 0.05 |
|   | Methyl p-benzoate | 0.1 |

Evaluation

Using the cosmetics of Examples 25 to 31 and Comparative Examples 5 to 7 on the faces of a panel of 10 members, useability tests were practiced. The test items are as shown below, and their evaluations are shown in Table 22.

(A) Ease of Coating on Face o: uniformly and well coated

Δ: slight superficial slippage, slightly irregular x: superficial slippage, coated with difficulty (B) Adhesion Feeling of Cosmetic to Skin o: good feeling Δ: slightly deficient feeling x: no good feeling (C) Fresh Feeling During Usage o: moderately fresh Δ: slightly sticky x: sticky

TABLE 22

| Product | Complex material amount (wt. %) | Evaluation of useability | | |
|---|---|---|---|---|
|   |   | A | B | C |
| (Present invention) |   |   |   |   |
| C-HL-1 | 0.3 | o | o | o |
| C-HE3-2 | 0.3 | o | o | o |
| C-NK-1 | 0.2 | o | o | o |
| C-HE3-22 | 0.2 | o | o | o |
| N-HK-1 | 0.3 | o | o | o |
| N-HE2-2 | 0.3 | o | o | o |
| F-HB-1 | 1 | o | o | o |
| F-HE3-2 | 1 | o | o | o |
| W-HS-1 | 0.2 | o | o | o |
| W-HE3-2 | 0.2 | o | o | o |
| A-HL-1 | 0.6 | o | o | o |
| A-HE3-2 | 0.6 | o | o | o |
| D-HL-1 | 0.2 | o | o | o |
| D-HE3-2 | 0.2 | o | o | o |
| (Comparative) |   |   |   |   |
| Example 5 | — | x | x | x |
| Example 6 | — | x | x | x |
| Example 7 | — | x | x | Δ |

As apparent from Table 22, the cosmetics of the present invention were found to have an excellent coating ease onto the face, adhesion to the skin, and were moderately fresh. They were also satisfactory in other useabilities demanded for cosmetics.

Example 32 (Preparation and Evaluation of Laxative)

Preparation of Complex Material-111

To a 2% aqueous solution of Hibis 104 was added a 2% aqueous dispersion of either one of Laponite XLG, Kunipia, Beagam, Smectone SA, bentonite of Japanese Pharmacopoeia as a water swellable silicate mineral to a weight fraction calculated on solids of Hibis 104 of 0.75, and after mixing uniformly by a homomixer, each mixture was adjusted to pH 6.3 with 2N NaOH. Next, under stirring, 2-fold amount of ethanol was added to each mixture, and the powder of the complex material was precipitated and recovered. Each of the precipitates recovered was vacuum dried at 60° C. for 16 hours to obtain various complex material powders (yields were all 90% or more).

Preparation of Complex Material-222

The preparation of Complex Material-111 was repeated except for using Aerosil #200, #300 and #380 as the above-mentioned water swellable silicate.

Preparation of Complex Material-333

Various complex material powders were obtained as in the Preparation of the complex material—3 of Example 18.

The respective complex materials obtained in the preparation methods as described above were each charged in an amount of 100 mg into 200 ml of pure water, Liquid 1 (artificial gastric juice) and Liquid 2 (artificial enteric juice) listed in Japanese Pharmacopoeia, the mixture was stirred with a magnetic stirrer for 30 minutes, left to stand for 24 hours, and then the volume of the complex material gel swelling was measured by a measuring cylinder. Table 23 summarizes the gel volumes of the respective complex materials.

TABLE 23

| Gel volumes of respective complex materials | | | |
|---|---|---|---|
|   | Gel volume | | |
| Complex material name | Pure water | Liquid 1 | Liquid 2 |
| Hibis 104/Laponite XLG | 110 | 1 or less | 15 |
| Hibis 104/Kunipia 102 | 102 | 1 or less | 17 |
| Hibis 104/Beagam | 108 | 1 or less | 12 |
| Hibis 104/Smectone SA | 104 | 1 or less | 18 |
| Hibis 104/Bentonite of Japanese Pharmacopoeia | 124 | 1 or less | 20 |
| Hibis 104/Aerosil #200 | 105 | 1 or less | 13 |
| Hibis 104/Aerosil #300 | 109 | 1 or less | 14 |
| Hibis 104/Aerosil #380 | 118 | 1 or less | 19 |
| Carboxymethyl cellulose/ Laponite XLG | 25 | 1 or less | 15 |
| Carboxymethyl cellulose/ Kunipia | 26 | 1 or less | 16 |
| Carboxymethyl cellulose/ Beagam | 27 | 1 or less | 16 |
| Carboxymethyl cellulose/ Smectone SA | 26 | 1 or less | 14 |
| Carboxymethyl cellulose/ Bentonite of Japanese Pharmacopoeia | 26 | 1 or less | 17 |

Toxicity Test

The above-mentioned respective complex materials were ingested by rat at doses of 2500 and 5000 mg/kg, and an observation was conducted over 30 days to determine the toxicity thereof with time. The only abnormality observed during this test period was a saturated state related to the dose administered.

Evaluation

A laxative with a recipe shown below was administered continuously between meals to 10 rabbits for one week. As a result, the number of discharges for one week increased, and by using either of the laxatives shown below containing the complex material of the present invention, it was confirmed that the quality of the feces can be commonly ameliorated.

(in one package)

Complex material* 400 mg

Plantago•Obata seed skin 200 mg

Carboxymethyl cellulose 100 mg

Sennoside 2 mg

Bisbenthiamine 1 mg

[*Hibis 104/bentonite of Japanese Pharmacopoeia complex material, Hibis 104/Aerosil #300 complex material or carboxymethyl cellulose/bentonite of Japanese Pharmacopoeia complex material). (Preparation and evaluation of rectal administration compositions)

Example 33

Preparation of Complex Material

Various complex material powders were prepared as in the preparation of the complex materials in Examples 18 to 32, and were respectively used in the rectal administration compositions shown below.

Example 34

An amount of 97.34 g of Wittepsol H-15 was melted by heating to about 65° C., and 0.33 g of hydrocortizone acetate and 2.33 g of the complex* were added thereto, followed by mixing under stirring. The mixture was injected into a suppository container in an amount of 1.5 g, and cooled to give a rectal administration composition of the present invention.

| *Complex material | Corresponding product |
|---|---|
| Hibis 104/Laponite | U-HL-1 |
| Hibis 104/Aerosil #300 | U-HE3-2 |
| Carboxymethyl cellulose/Laponite | U-CML-3 |

Comparative Example 8

An amount of 99.67 g of Wittepsol H-15 was melted by heating to about 65° C., and 0.33 g of hydrocortizone acetate was added thereto, followed by mixing under stirring. The mixture was injected into a suppository container in an amount of 1.5 g, and cooled to give a rectal administration composition.

Comparative Example 9

An amount of 97.34 g of Wittepsol H-15 was melted by heating to about 65° C., and 0.33 g of hydrocortizone acetate and 2.33 g of Laponite were added thereto, followed by mixing under stirring. The mixture was injected into a suppository container in an amount of 1.5 g, and cooled to give a rectal administration composition.

Comparative Example 10

An amount of 97.34 g of Wittepsol H-15 was melted by heating to about 65° C., and 0.33 g of hydrocortizone acetate and 2.33 g of sodium polyacrylate were added thereto, followed by mixing under stirring. The mixture was injected into a suppository container in an amount of 1.5 g, and cooled to give a rectal administration composition.

Suppository Release Test

For an examination of the releasability and persistency of the rectal administration compositions U-HL-1, U-HE3-2, and U-CML-3 derived from Example 34 and Comparative Examples 8 to 10, release tests were practiced by using a suppository release tester TMS-103 Model (Toyama Sangyo). Table 24 summarizes the change with lapse of time of the release ratio (%) of hydrocortizone acetate. From this Table, it can be seen that the rectal administration composition of the present invention exhibits a high releasability, and further, supplies a constant drug level over a long time, thus also having an excellent persistency.

TABLE 24

Suppository release test results

| Time elapsed (min.) | Release ratio of hydrocortizone acetate (%) | | | | | |
|---|---|---|---|---|---|---|
| | U-HL-1 | U-HE3-2 | U-CML-3 | Comparative Ex. 8 | Ex. 9 | Ex. 10 |
| 0 | 0 | 0 | 0 | 0 | 0 | 0 |
| 30 | 13 | 14 | 9 | 3 | 6 | 5 |
| 60 | 18 | 19 | 15 | 5 | 10 | 8 |
| 120 | 27 | 28 | 23 | 12 | 17 | 14 |
| 240 | 39 | 40 | 33 | 20 | 28 | 25 |
| 360 | 48 | 50 | 41 | 25 | 36 | 33 |
| 480 | 55 | 57 | 47 | 29 | 40 | 37 |

The following rectal administration compositions were obtained according to the recipes shown below, and in all thereof, an excellent releasability and persistency were confirmed.

Example 35

An amount of 84.09 g of Wittepsol H-15 and 0.6 g of stearic acid were melted by heating at about 45° C., and 0.33 g of hydrocortizone acetate, 4.0 g of lidocaine, 0.66 g of methylphedrine hydrochloride, 1.33 g of allantoin, 0.66 g of diphenhydramine hydrochloride, 3.33 g of tocopherol acetate and each 5.00 g of above-mentioned three kinds of complex materials were added thereto, followed by mixing under stirring. The mixture was injected into a suppository container in an amount of 1.5 g and cooled to room temperature to obtain a rectal administration composition of the present invention.

Example 36

An amount of 70.0 g of Pharmasol B-105, 10.0 g of Pharmasol N-145 and 11.0 g of Pharmasol A-105 were melted by heating at about 75° C., and 6.66 g of indomethacin and each 2.34 g of Hibis 104/Kunipia complex material, Hibis 104/Aerosil #380 complex material or carboxymethyl cellulose/Kunipia complex material were added thereto, followed by mixing under stirring. The mixture was injected into a suppository contained in an amount of 1.65 g and cooled to room temperature to obtain a rectal administration composition of the present invention.

Example 37

An amount of 42.0 g of Wittepsol H-15 and 15.0 g of Wittepsol E-75 were melted by heating at about 75° C., and 3.0 g of Bleomycin hydrochloride, 10.0 g of Panacete 875 and each 30.0 g of Hibis 104/Smectone complex material, Hibis 104/Aerosil #200 complex material or carboxymethyl cellulose/Smectone complex material were added thereto, followed by mixing under stirring. The mixture was injected into a container in an amount of 1.4 g and cooled to room temperature to obtain a rectal administration composition of the present invention. (Preparation and evaluation of pharmaceutical composition)

Example 38

Inclusion of Difficult-to-Solubilize Pharmaceutical

In this Example, the respective complex materials obtained in Example 33 were employed.

An amount of 0.5 g of griseofulvin was dissolved in 100 ml of acetone, 9.5 g of complex material* was dispersed into the solution. After a thorough stirring, acetone was evaporated by an evaporator, and sufficiently dried to give a pharmaceutical-included complex material containing 5% of griseofulvin included therein.

| *Complex material | Corresponding product |
|---|---|
| Hibis 104/Laponite | I-HL-1 |
| Hibis 104/Aerosil #300 | I-HE3-2 |
| Carboxymethyl cellulose/Laponite | I-CML-3 |

Figure 5:
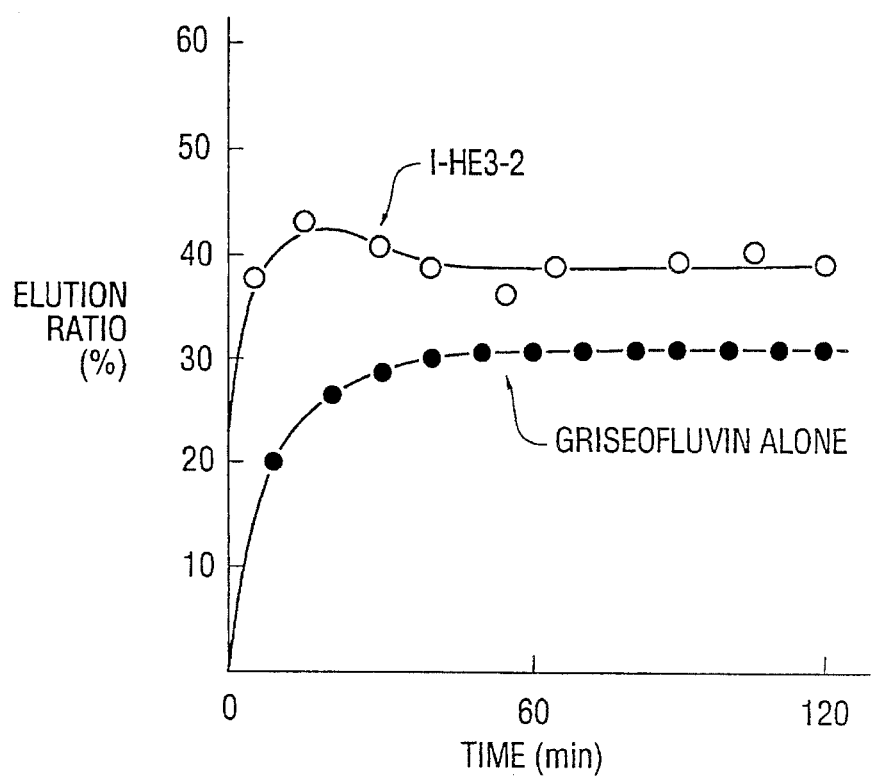
FIG. 5 and FIG. 6 are graphs showing elution ratios of difficult-to-solubilize pharmaceutical from the pharmaceutical included complexes (I-HE3-2) and (I-CML-3) of Example 39, respectively.

Solubility Test (1) The pharmaceutical-included complex material obtained in Example 38 was weighed to 5 mg as griseofulvin, and the amount of griseofulvin dissolved in water was examined with a lapse of time by measuring the absorbance at 295 nm. The test temperature was made 37° C., and the solvent amount one liter. As a control, griseofulvin alone was weighed in an amount of 5 mg, and the change in amount dissolved with a lapse of time was monitored. The results for I-HL-1 are shown in Table 25, and those for I-HE3-2 in FIG. 5.

TABLE 25

| | Change in solubility with lapse of time | |
|---|---|---|
| | Amount dissolved | |
| Time (min.) | I-HL-1 | Pharmaceutical alone |
| 0 | 0 | 0 |
| 3 | 21 | 18 |

TABLE 25-continued

| | Change in solubility with lapse of time | |
|---|---|---|
| | Amount dissolved | |
| Time (min.) | I-HL-1 | Pharmaceutical alone |
| 6 | 35 | 24 |
| 10 | 51 | 26 |
| 15 | 53 | 27 |
| 20 | 55 | 28 |
| 30 | 55 | 28 |
| 60 | 55 | 28 |

Figure 6:
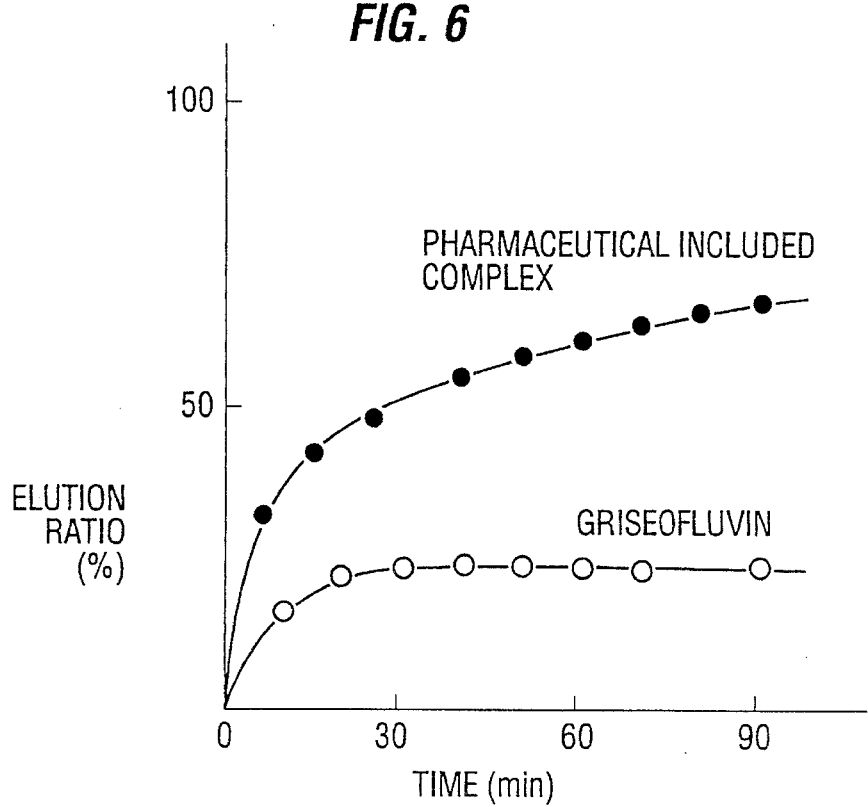

(2) The I-CML-3 included a complex material was weighed to 25 mg as griseofulvin, dispersed into 500 ml of Liquid 2 of Japanese Pharmacopoeis (pH 6.8), and the change with a lapse of time of the elution ratio of griseofulvin at 37° C. was measured at an absorbance of 295 nm by an absorption photometer. For comparison, the elution ratio was also measured for the case when only 25 mg of griseofulvin was measured. The results are shown in FIG. 6. As can be seen from the results, the pharmaceutical included complex material has a higher solubility in water compared with the system of griseofulvin alone.

From these results, it can be appreciated that the pharmaceutical-included complex material has an increased solubility in water by about 2-fold, as compared with the system of griseofulvin alone. The griseofulvin treated with Laponite itself which has a pharmaceutical-including ability showed substantially no significant difference from the system of griseofulvin alone.

Example 39 Oily Ointment

Petrolatum and fluid paraffin were mixed and melted at 70° C., and to the mixture was added the pharmaceutical-included complex material* prepared in Example 38 (containing 5% by weight of griseofulvin), followed by thorough mixing to obtain an oily ointment. In the following, the amounts formulated are all % by weight.

| Pharmaceutical-included complex material obtained in Example 38 | 4.0 |
|---|---|
| Petrolatum | 79.0 |
| Fluid paraffin | 17.0 |
| *Pharmaceutical-included complex material | Oily ointment |
| I-HL-1 | O-HL-1 |
| I-HE3-2 | O-HE3-2 |
| I-CML-3 | O-CML-3 |

Comparative Example 11

For comparison of Example 39, an oily ointment was similarly obtained with the recipe shown below.

| Griseofulvin | 0.2 |
|---|---|
| Petrolatum | 79.0 |
| Fluid paraffin | 20.8 |

Therapeutical Test

For an examination of the therapeutical effects of the oily ointments of Example 39 and Comparative Example 11, a panel of 30 members afflicted with tinia pedis were coated with the ointment once per day, and the afflicted portions were observed over two weeks. A judgement was conducted according to the following standards. The results are shown in Table 26.

Remarkably effective: remarkable improvement recognized
Effective: considerable improvement recognized
Slightly effective: improvement recognized
Ineffective: no improvement recognized
Worsening: worsening recognized

TABLE 26

(Unit: members)

| Judgement | After 3 days | | | | After 7 days | | | | After 14 days | | | |
|---|---|---|---|---|---|---|---|---|---|---|---|---|
| | O-HL-1 | O-HE3-2 | O-CML-3 | Com. ex. 1 | O-HL-1 | O-HE3-2 | O-CML-3 | Com. ex. 1 | O-HL-1 | O-HE3-2 | O-CML-3 | Com. ex. 1 |
| Remarkably effective | 9 | 10 | 10 | 2 | 10 | 11 | 11 | 4 | 12 | 13 | 12 | 7 |
| Effective | 6 | 5 | 5 | 6 | 5 | 4 | 4 | 5 | 3 | 3 | 3 | 5 |
| Slightly effective | 0 | 0 | 0 | 5 | 0 | 0 | 0 | 5 | 0 | 0 | 0 | 5 |
| Ineffective | 0 | 0 | 0 | 2 | 0 | 0 | 0 | 1 | 0 | 0 | 0 | 0 |
| Worsening | 0 | 0 | 0 | 0 | 0 | 0 | 0 | 0 | 0 | 0 | 0 | 0 |

From the results of Table 26, it is suggested that the pharmaceutical composition of the present invention had an excellent therapeutical effect on tinia pedis.

Example 40 Creamy Pharmaceutical

Three kinds of creamy pharmaceuticals were prepared in conventional manner.

| | |
|---|---|
| Pharmaceutical-included complex material obtained in Example 38 (containing 5% of griseofulvin) | 4.0 |
| Cetostearyl alcohol | 3.5 |
| Squalane | 40.0 |
| Honeywax | 3.0 |
| Reduced lanolin | 5.0 |
| Ethyl p-benzoate | 0.3 |
| Polyoxyethylene (20) sorbitane | 2.0 |
| Monopalmitic acid ester | 2.0 |
| Stearic acid monoglyceride | 2.0 |
| Retinol acetate | 2.0 |
| Perfume | 0.03 |
| 1,3-Butylene glycol | 5.0 |
| Glycerine | 5.0 |
| Purified water | balance |

Example 41 Milky Lotion Pharmaceutical

Three kinds of milky lotion pharmaceuticals were prepared in conventional manner.

| | |
|---|---|
| Pharmaceutical-included complex material obtained in Example 38 (containing 5% of griseofulvin) | 4.0 |
| Stearic acid | 1.5 |
| Cetyl alcohol | 0.5 |
| Honeywax | 2.0 |
| Polyoxyethylene (10) | 1.0 |
| Monooleic acid ester | 2.0 |
| Sodium hyarulonate | 0.1 |
| Propylene glycol | 5.0 |
| Ethanol | 3.0 |
| Ethyl p-benzoate | 0.3 |
| Perfume | 0.33 |
| Purified water | balance |

(Preparation and evaluation of external skin ulcer agent)

Example 42

An amount of 30 parts by weight of the complex material* was formulated with 10 parts by weight of Coridone iodine (produced by BASF), 35 parts by weight of petrolatum of Japanese Pharmacopoeia and 25 parts by weight of a fluid paraffin to prepare an external skin ulcer ointment.

*Complex material of Example 1 (polymer weight fraction=0.5),

Complex material of Example 3 (polymer weight fraction=0.5),

Complex material of Example 2 (polymer weight fraction=0.3).

When the ointment was coated on the acetate ulcer about 2 cm square formed at the back of a guinea pig 6 weeks old, the ulcer portion was moderately dried and healed one week later by an administration of either pharmaceutical.

Also, by use of the above-mentioned complex materials, the three following kinds of external skin ulcer agents were prepared for each material.

Example 43 O/W Cream

| | (wt. parts) |
|---|---|
| Each complex material used in Example 42 | 30 |
| Petrolatum of Japanese Pharmacopocia | 15 |
| Olive oil | 10 |
| Squalane | 22.49 |
| Sucrose fatty acid ester | 2.5 |
| Glycerine | 10 |
| Purified water | 10 |
| Benzalkonium chloride | 0.01 |

Example 44 Powder

| | (wt. parts) |
|---|---|
| Hibis 104/Laponite XLG complex material | 40 |
| Kaolin | 25 |
| Spherical silica | 33 |
| Glycyrrhizinic acid | 2 |

Example 45 Aerosol

| | (wt. parts) |
|---|---|
| Freon (propellant) | 70 |

-continued

| | (wt. parts) |
|---|---|
| LPG (propellant) | 23.9 |
| Hibis 104/Laponite XLG complex material | 5 |
| Spherical silica | 1 |
| Silicon | 0.1 |

Example 46 W/O Cream

| | (wt. parts) |
|---|---|
| Petrolatum of Japanese Pharmacopoeia | 40 |
| Cetanol | 18 |
| Sorbitane sesquioleate | 5 |
| Lauromacrogall | 0.5 |
| Vitamin E acetate | 0.5 |
| Hibis 104/Laponite XLG complex material | 20 |
| Purified water | 16 |

UTILIZABILITY IN INDUSTRY

The complex material of the present invention, as descried above, has a very high water swellability and gel strength in combination, and yet has an affinity for living bodies, and further, can be provided as a material having a high safety to living bodies, by choosing the starting material. Therefore, it can be utilized in industrial fields to which pharmaceuticals and cosmetics belong, as a matter of course, and many other applications are possible, including sanitary uses such as paper diapers, sanitary goods, soil improvers for afforestation agriculture and horticulture, water stoppage agents, plasma fractionating agents, dust preventives, dew formation preventives, deodorants, disposable pocked heaters, and gels for artificial seeds, etc.

In the following, the specific features of the present invention are described in more detail, and those skilled in the art will easily find the fields of utilization for the complex material of the present invention other than those as described above, from these descriptions.

First, the gel-like aromatic composition formulated with the above-described complex material has an excellent stability, and a good perfume generation without a lowering of the volatilization of the perfume with a lapse of time.

Also, when the complex material is formulated as the thickener of a cosmetic, it is free from stickiness, gives a conspicuous feeling of freshness, and has an excellent stability. Further, in a system formulated a polymer derived from living body such as collagen or hyaluronic acid which has been recently used as the humectant, the drawbacks of a difficult coatability on account of stickiness or absence of a good feeling on account of a superficial slippage can be improved by a formulation of the complex material.

The laxative formulated with the complex material can reduce the dose as a whole, and particularly, in the initial stage of therapy, does not worsen flatulence customarily accompanying constipation, but rather suppresses such an unpleasant phenomenon. Further, it will not ooze out of the anus as in the case of the laxative therapy using a fluid paraffin as the main component.

Further, the rectal administration composition of the present invention is a novel base for a suppository formulated with the above-mentioned complex material. The base enhances the releasability of the pharmaceutical, and exhibits an excellent residence within the rectal cavity, whereby a biological utilization efficiency of the drug is also enhanced. Further, since it resides within the rectal cavity for a long time, the persistency of the pharmaceutical effect can be increased.

Also, in the pharmaceutical composition of the present invention, a formulation of a difficult-to-solubulize pharmaceutical in the above-mentioned complex material remarkably increases the solubility of the difficult-to-solubulize pharmaceutical in water, whereby a permucosal and percutaneous absorption can be improved.

The external skin ulcer agent of the present invention, by a formulation of the above-mentioned complex material, has the function of sufficiently absorbing the oozed fluid while maintaining the skin ulcer portion at an adequate equilibrated water content, and further, has the function of protecting the ulcer portion through an absorption of the oozed fluid, which becomes an elastic gel. At the same time, the pharmaceutical formulated is gradually released accompanied by an absorption of the oozed fluid, whereby the effect can persist for a long time.

We claim:

1. A composite of a hydrophilic polymer-silicate mineral comprising a carboxyl group-containing hydrophilic polymer and a water swellable silicate mineral, said composite having an absorption spectrum not present in either the starting carboxyl group-containing hydrophilic polymer or the water swellable silicate mineral within the IR-ray absorption spectrum of 1000 to 1300 cm$^{-1}$.

2. A composite according to claim 1, wherein the carboxyl group-containing hydrophilic polymer is selected from the group consisting of acrylic polymers of poly(acrylic acid) or poly (methacrylic acid), carboxymethyl cellulose, hyaluronic acid, xanthan gum, gum arabic, and alginic acid.

3. A composite according to claim 1, wherein the water swellable silicate mineral is a fine silica flour or a silicate mineral of layer structure.

4. A composite according to claim 1, wherein the carboxyl group-containing hydrophilic polymer and the water swellable silicate mineral are selected from the group of combinations consisting of an acrylic acid polymer and a layered silicate mineral, an acrylic acid polymer and a swellable fine silica flour, and a polysaccharide and a layered silicate mineral, having, respectively, gel strengths of 15,700 to 127,000 dyne/cm$^2$, 9800 to 118,000 dyne/cm$^2$, and 1960 to 58,000 dyne/cm$^2$ when dispersed in purified water to a concentration of 1% by weight.

5. A composite according to claim 1, wherein the carboxyl group-containing hydrophilic polymer is an acrylic acid type polymer having a molecular weight of about 1,000,000 to about 4,000,000 and the water swellable silicate mineral is fine silica flour or a silicate mineral of layered structure, wherein said composite is prepared from a gel comprising said acrylic acid type polymer and said silica flour or silicate mineral of layered structure at pH 6.0 to 6.5.

6. A composite according to claim 1, wherein the carboxyl group-containing hydrophilic polymer is a crosslinked polyacrylic acid and the water swellable silicate mineral is a swellable particulate silica, wherein said composite is prepared from a gel comprising a crosslinked polyacrylic acid and a swellable particulate silica at a pH of 6.0 to 6.5.

7. A composite according to claim 1, wherein the carboxyl group-containing hydrophilic polymer is a crosslinked polyacrylic acid and the water swellable silicate mineral is a layered silicate mineral, wherein said composite is prepared from a gel comprising a crosslinked polyacrylic acid and a layered silicate mineral at a pH of 6.0 to 6.5.

8. A gel flavoring composition comprising 0.1 to 90% by weight of a composite according to claim 1 and 1 to 99.0% by weight of a perfume, 0 to 90% by weight of an organic solvent, 0 to 40% by weight of a nonionic surfactant, and the remainder is water.

9. A cosmetic comprising a composite according to claim 1 formulated with a thickener.

10. A laxative comprising a composite according to claim 1.

11. A rectal composition comprising a composite according to claim 1.

12. A pharmaceutical composition comprising a composite according to claim 1.

13. A skin ulcer agent comprising a composite according to claim 1.

* * * * *